United States Patent
Lipkens et al.

(10) Patent No.: US 10,370,635 B2
(45) Date of Patent: *Aug. 6, 2019

(54) ACOUSTIC SEPARATION OF T CELLS

(71) Applicant: FloDesign Sonics, Inc., Wilbraham, MA (US)

(72) Inventors: Bart Lipkens, Hampden, MA (US); Rudolf Gilmanshin, Framingham, MA (US); Brian Dutra, East Longmeadow, MA (US); Benjamin Ross-Johnsrud, Springfield, MA (US)

(73) Assignee: FloDesign Sonics, Inc., Wibraham, MA (US)

( * ) Notice: Subject to any disclaimer, the term of this patent is extended or adjusted under 35 U.S.C. 154(b) by 246 days.

This patent is subject to a terminal disclaimer.

(21) Appl. No.: 15/417,172

(22) Filed: Jan. 26, 2017

(65) Prior Publication Data

US 2017/0218323 A1    Aug. 3, 2017

Related U.S. Application Data

(63) Continuation-in-part of application No. 15/139,248, filed on Apr. 26, 2016, now Pat. No. 9,738,866.
(Continued)

(51) Int. Cl.
*B01D 17/04* (2006.01)
*C12M 1/00* (2006.01)
(Continued)

(52) U.S. Cl.
CPC ............ *C12M 47/02* (2013.01); *B01D 17/04* (2013.01); *B01D 17/06* (2013.01); *B01D 21/283* (2013.01);
(Continued)

(58) Field of Classification Search
CPC ...... B01D 29/115; B01D 37/00; B01D 29/52; B01D 29/865; B01D 2201/0415;
(Continued)

(56) References Cited

U.S. PATENT DOCUMENTS 2,473,971 A    6/1949    Ross
2,667,944 A    2/1954    Crites
(Continued)

FOREIGN PATENT DOCUMENTS

DE    30 27 433 A1    2/1982
DE    32 18 488 A1    11/1983
(Continued)

OTHER PUBLICATIONS

Grenvall et al.; Concurrent Isolation of Lymphocytes and Granulocytes Using Prefocused Free Flow Acoustophoresis; Analytical Chemistry; vol. 87; pp. 5596-5604; 2015.
(Continued)

*Primary Examiner* — Walter D. Griffin
*Assistant Examiner* — Cameron J Allen
(74) *Attorney, Agent, or Firm* — Richard M. Klein, Esq.; Fay Sharpe, LLP

(57) ABSTRACT

Acoustophoretic devices and methods for separating biological cells (particularly T-cells) from other fluids/materials using multi-dimensional acoustic standing waves are disclosed. The devices include an inlet, at least two outlets, and a flow chamber having an ultrasonic transducer-reflector pair. Specifically, T cells, B cells, or NK cells can be separated from other blood components. A dual-pass acoustophoretic system including two acoustophoretic devices arranged in series and fluidly connected to one another is also illustrated. Means for pre-chilling the mixture prior to
(Continued)

separation in the devices or system can be used to improve retention, concentration, and clarification and to prevent outgassing.

18 Claims, 17 Drawing Sheets

Related U.S. Application Data which is a continuation-in-part of application No. 14/975,307, filed on Dec. 18, 2015, now Pat. No. 9,822,333, which is a continuation-in-part of application No. 14/175,766, filed on Feb. 7, 2014, now Pat. No. 9,416,344, which is a continuation-in-part of application No. 14/026,413, filed on Sep. 13, 2013, now Pat. No. 9,458,450, which is a continuation-in-part of application No. 13/844,754, filed on Mar. 15, 2013, now Pat. No. 10,040,011.

(60) Provisional application No. 62/286,984, filed on Jan. 26, 2016, provisional application No. 62/256,952, filed on Nov. 18, 2015, provisional application No. 62/243,211, filed on Oct. 19, 2015, provisional application No. 62/211,057, filed on Aug. 28, 2015, provisional application No. 62/093,491, filed on Dec. 18, 2014, provisional application No. 61/761,717, filed on Feb. 7, 2013, provisional application No. 61/708,641, filed on Oct. 2, 2012, provisional application No. 61/754,792, filed on Jan. 21, 2013, provisional application No. 61/708,641, filed on Oct. 2, 2012, provisional application No. 61/611,159, filed on Mar. 15, 2012, provisional application No. 61/611,240, filed on Mar. 15, 2012.

(51) Int. Cl.
| | | |
|---|---|---|
| *B01D 21/28* | (2006.01) | |
| *C12N 13/00* | (2006.01) | |
| *C12M 1/34* | (2006.01) | |
| *G10K 9/122* | (2006.01) | |
| *B01D 17/06* | (2006.01) | |
| *B06B 1/06* | (2006.01) | |
| *C12M 1/26* | (2006.01) | |
| *C12M 1/42* | (2006.01) | |

(52) U.S. Cl.
CPC ........... *B06B 1/0644* (2013.01); *C12M 29/10* (2013.01); *C12M 29/18* (2013.01); *C12M 33/08* (2013.01); *C12M 35/04* (2013.01); *C12M 41/12* (2013.01); *C12N 13/00* (2013.01); *G10K 9/122* (2013.01)

(58) Field of Classification Search
CPC ...... B01D 2201/0446; B01D 2201/127; B01D 17/04; B01D 21/283; B01D 17/06; C12M 47/02; C12M 29/18; C12M 23/22; C12M 29/10; C12M 33/08; C12M 35/04; C12N 13/00; B06B 1/0644; H01L 41/0973
See application file for complete search history.

(56) References Cited

U.S. PATENT DOCUMENTS

| | | | |
|---|---|---|---|
| 3,372,370 | A | 3/1968 | Cyr |
| 3,555,311 | A | 1/1971 | Weber |
| 4,055,491 | A | 10/1977 | Porath-Furedi |
| 4,065,875 | A | 1/1978 | Srna |
| 4,118,649 | A | 10/1978 | Schwartzman et al. |
| 4,158,629 | A | 6/1979 | Sawyer |
| 4,165,273 | A | 8/1979 | Azarov et al. |
| 4,173,725 | A | 11/1979 | Asai et al. |
| 4,204,096 | A | 5/1980 | Barcus et al. |
| 4,254,661 | A | 3/1981 | Kossoff et al. |
| 4,320,659 | A | 3/1982 | Lynnworth et al. |
| 4,344,448 | A | 8/1982 | Potts |
| 4,398,325 | A | 8/1983 | Piaget et al. |
| 4,552,669 | A | 11/1985 | Sekellick |
| 4,666,595 | A | 5/1987 | Graham |
| 4,673,512 | A | 6/1987 | Schram |
| 4,699,588 | A | 10/1987 | Zinn et al. |
| 4,743,361 | A | 5/1988 | Schram |
| 4,759,775 | A | 7/1988 | Peterson et al. |
| 4,800,316 | A | 1/1989 | Wang |
| 4,821,838 | A | 4/1989 | Chen |
| 4,836,684 | A | 6/1989 | Javorik et al. |
| 4,860,993 | A | 8/1989 | Goode |
| 4,878,210 | A | 10/1989 | Mitome |
| 4,983,189 | A | 1/1991 | Peterson et al. |
| 5,059,811 | A | 10/1991 | King et al. |
| 5,062,965 | A | 11/1991 | Bernou et al. |
| 5,085,783 | A | 2/1992 | Feke et al. |
| 5,164,094 | A | 11/1992 | Stuckart |
| 5,225,089 | A | 7/1993 | Benes et al. |
| 5,371,729 | A | 12/1994 | Manna |
| 5,395,592 | A | 3/1995 | Bolleman et al. |
| 5,431,817 | A | 7/1995 | Braatz et al. |
| 5,443,985 | A | 8/1995 | Lu et al. |
| 5,452,267 | A | 9/1995 | Spevak |
| 5,475,486 | A | 12/1995 | Paoli |
| 5,484,537 | A | 1/1996 | Whitworth |
| 5,527,460 | A | 6/1996 | Trampler et al. |
| 5,560,362 | A | 10/1996 | Sliwa, Jr. et al. |
| 5,594,165 | A | 1/1997 | Madanshetty |
| 5,604,301 | A | 2/1997 | Mountford et al. |
| 5,626,767 | A | 5/1997 | Trampler et al. |
| 5,688,405 | A | 11/1997 | Dickinson et al. |
| 5,711,888 | A | 1/1998 | Trampler et al. |
| 5,831,166 | A | 11/1998 | Kozuka et al. |
| 5,834,871 | A | 11/1998 | Puskas |
| 5,902,489 | A | 5/1999 | Yasuda et al. |
| 5,912,182 | A | 6/1999 | Coakley et al. |
| 5,947,299 | A | 9/1999 | Vazquez et al. |
| 5,951,456 | A | 9/1999 | Scott |
| 6,090,295 | A | 6/2000 | Raghavarao et al. |
| 6,166,231 | A | 12/2000 | Hoeksema |
| 6,216,538 | B1 | 4/2001 | Yasuda et al. |
| 6,205,848 | B1 | 6/2001 | Faber et al. |
| 6,273,262 | B1 | 8/2001 | Yasuda et al. |
| 6,332,541 | B1 | 12/2001 | Coakley et al. |
| 6,391,653 | B1 | 5/2002 | Letcher et al. |
| 6,475,151 | B2 | 11/2002 | Koger et al. |
| 6,482,327 | B1 | 11/2002 | Mod et al. |
| 6,487,095 | B1 | 11/2002 | Malik et al. |
| 6,592,821 | B1 | 7/2003 | Wada et al. |
| 6,641,708 | B1 | 11/2003 | Becker et al. |
| 6,649,069 | B2 | 11/2003 | DeAngelis |
| 6,699,711 | B1 | 3/2004 | Hahn et al. |
| 6,727,451 | B1 | 4/2004 | Fuhr et al. |
| 6,763,722 | B2 | 7/2004 | Fjield et al. |
| 6,881,314 | B1 | 4/2005 | Wang et al. |
| 6,929,750 | B2 | 8/2005 | Laurell et al. |
| 6,936,151 | B1 | 8/2005 | Lock et al. |
| 7,008,540 | B1 | 3/2006 | Weavers et al. |
| 7,010,979 | B2 | 3/2006 | Scott |
| 7,061,163 | B2 | 6/2006 | Nagahara et al. |
| 7,081,192 | B1 | 7/2006 | Wang et al. |
| 7,093,482 | B2 | 8/2006 | Berndt |
| 7,108,137 | B2 | 9/2006 | Lal et al. |
| 7,150,779 | B2 | 12/2006 | Meegan, Jr. |
| 7,186,502 | B2 | 3/2007 | Vesey |
| 7,191,787 | B1 | 3/2007 | Redeker et al. |
| 7,322,431 | B2 | 1/2008 | Ratcliff |
| 7,331,233 | B2 | 2/2008 | Scott |
| 7,340,957 | B2 | 3/2008 | Kaduchak et al. |
| 7,373,805 | B2 | 5/2008 | Hawkes et al. |
| 7,541,166 | B2 | 6/2009 | Belgrader et al. |
| 7,601,267 | B2 | 10/2009 | Haake et al. |
| 7,673,516 | B2 | 3/2010 | Janssen et al. |

(56) References Cited

U.S. PATENT DOCUMENTS

| | | |
|---|---|---|
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugharn, Jr. et al. |
| 2014/0319077 A1 | 10/2014 | Lipkens et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0321129 A1 | 11/2015 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |

(56) References Cited

U.S. PATENT DOCUMENTS

| | | | |
|---|---|---|---|
| 2016/0237394 A1 | 8/2016 | Lipkens et al. | |
| 2016/0237395 A1 | 8/2016 | Lipkens et al. | |
| 2016/0252445 A1 | 9/2016 | Yu et al. | |
| 2016/0279540 A1 | 9/2016 | Presz, Jr. et al. | |
| 2016/0279551 A1 | 9/2016 | Foucault | |
| 2016/0312168 A1 | 10/2016 | Pizzi | |
| 2016/0314868 A1 | 10/2016 | El-Zahab et al. | |
| 2016/0319270 A1 | 11/2016 | Lipkens et al. | |
| 2016/0325206 A1 | 11/2016 | Presz, Jr. et al. | |
| 2016/0332159 A1 | 11/2016 | Dual et al. | |
| 2016/0339360 A1 | 11/2016 | Lipkens et al. | |
| 2016/0347628 A1 | 12/2016 | Dionne et al. | |
| 2016/0355776 A1 | 12/2016 | Lipkens et al. | |
| 2016/0361670 A1 | 12/2016 | Lipkens et al. | |
| 2016/0363579 A1 | 12/2016 | Lipkens et al. | |
| 2018/0298371 A1* | 10/2018 | Lipkens | B01L 3/502761 |

FOREIGN PATENT DOCUMENTS

| | | |
|---|---|---|
| DE | 196 48 519 A1 | 6/1998 |
| DE | 103 19 467 B3 | 7/2004 |
| DE | 10 2008 006 501 A1 | 9/2008 |
| EP | 0 292 470 B1 | 11/1988 |
| EP | 0 641 606 | 3/1995 |
| EP | 1 175 931 A1 | 1/2002 |
| EP | 1 254 669 B1 | 11/2002 |
| GB | 2 420 510 A | 5/2006 |
| JP | 9-136090 | 5/1997 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 97/34643 | 9/1997 |
| WO | WO 1998/017373 | 4/1998 |
| WO | WO 98/50133 A1 | 11/1998 |
| WO | WO 02/072234 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043297 A1 | 3/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |

OTHER PUBLICATIONS

International Search Report and Written Opinion for International Application No. PCT/US2017/015197 dated Apr. 3, 2017.
Alvarez et al.; Shock Waves, vol. 17, No. 6, pp. 441-447, 2008.
Benes et al.; Ultrasonic Separation of Suspended Particles, 2001 IEEE Ultrasonics Symposium; Oct. 7-10, 2001; pp. 649-659; Atlanta, Georgia.
Castilho et al.; Animal Cell Technology: From Biopharmaceuticals to Gene Therapy; 11—Animal Cell Separation; 2008.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Separation of bacterial spores from flowering water in macro-scale cavities by ultrasonic standing waves; submitted/uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-1196; 2012.
Annex to Form PCT/ISA/206—Communication Relating to the Results of the Partial International Search Report, dated Jul. 18, 2013.
European Search Report of European Application No. 11769474.5, dated Sep. 5, 2013.
European Search Report of European Application No. 13760840.2, dated Feb. 4, 2016.

(56) References Cited

OTHER PUBLICATIONS

European Search Report of European Application No. 13721179.3 dated Feb. 23, 2016.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2012/051804 dated Nov. 16, 2012.
International Search Report and Written Opinion of International Application No. PCT/US2013/037404 dated Jun. 21, 2013.
International Search Report and Written Opinion of International Application No. PCT/US2013/032705 dated Jul. 26, 2013.
International Search Report and Written Opinion of International Application No. PCT/US2013/050729 dated Sep. 25, 2013.
International Search Report dated Feb. 18, 2014 in corresponding PCT Application No. PCT/US2013/059640.
International Search Report for corresponding PCT Application Serial No. PCT/US2014/015382 dated May 6, 2014.
International Search Report for PCT/US2014/035557 dated Aug. 27, 2014.
International Search Report for PCT/US2014/043930 dated Oct. 22, 2014.
International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report dated Jul. 30, 2015 for International Application No. PCT/US2015/030009.
International Search Report for PCT/US2015/039125 dated Sep. 30, 2015.
International Search Report and Written Opinion for PCT Application Serial No. PCT/US2015/053200 dated Dec. 28, 2015.
European Search Report of European Application No. 11796470.0 dated Jan. 5, 2016.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/044586 dated Oct. 21, 2016.
International Search Report and Written Opinion for International Application No. PCT/US2016/031357 dated Jul. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.

* cited by examiner

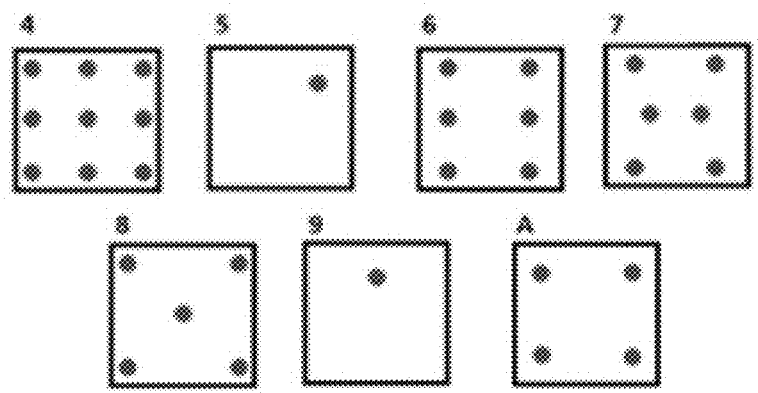
FIG. 15A
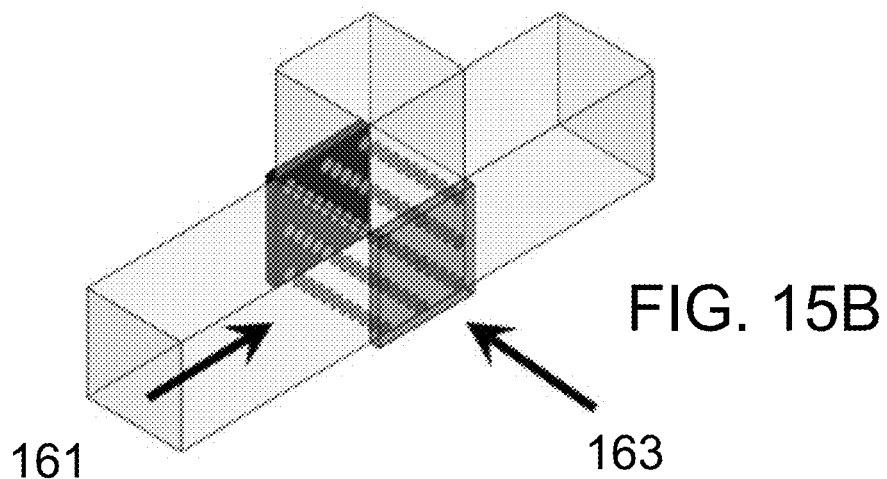
FIG. 15B
161          163
FIG. 15C          FIG. 15D
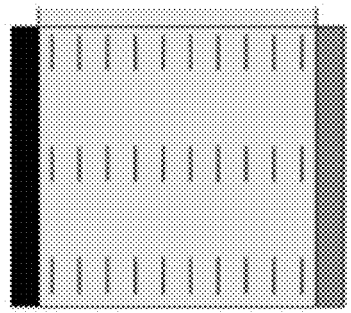   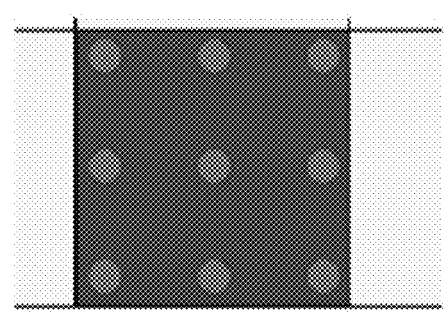

ACOUSTIC SEPARATION OF T CELLS

CROSS-REFERENCE TO RELATED APPLICATIONS

This application claims priority to U.S. Provisional Patent Application Ser. No. 62/286,984, filed on Jan. 26, 2016. This application is also a continuation-in-part of U.S. patent application Ser. No. 15/139,248, filed on Apr. 26, 2016, which was a continuation-in-part of U.S. patent application Ser. No. 14/975,307, filed Dec. 18, 2015, which claims priority to U.S. Provisional Patent Application Ser. No. 62/256,952, filed on Nov. 18, 2015, and to U.S. Provisional Patent Application Ser. No. 62/243,211, filed on Oct. 19, 2015, and to U.S. Provisional Patent Application Ser. No. 62/211,057, filed on Aug. 28, 2015, and to U.S. Provisional Patent Application Ser. No. 62/093,491, filed on Dec. 18, 2014. U.S. patent application Ser. No. 14/975,307 is also a continuation-in-part of U.S. patent application Ser. No. 14/175,766, filed on Feb. 7, 2014, which claims priority to U.S. Provisional Patent Application Ser. No. 61/761,717, filed on Feb. 7, 2013, and is also a continuation-in-part of U.S. patent application Ser. No. 14/026,413, filed on Sep. 13, 2013, which claims the benefit of U.S. Provisional Patent Application Ser. No. 61/708,641, filed on Oct. 2, 2012. U.S. patent application Ser. No. 14/026,413 is also a continuation-in-part of U.S. Ser. No. 13/844,754, filed Mar. 15, 2013, which claims the benefit of U.S. Provisional Patent Application Ser. No. 61/754,792, filed Jan. 21, 2013, and of U.S. Provisional Patent Application Ser. No. 61/708,641, filed Oct. 2, 2012, and of U.S. Provisional Patent Application Ser. No. 61/611,159, filed Mar. 15, 2012, and of U.S. Provisional Patent Application Ser. No. 61/611,240, filed Mar. 15, 2012. These applications are incorporated herein by reference in their entireties.

BACKGROUND

The human blood system contains many different cell types with different functions. The cells in the blood are typically broken down into three types: red blood cells or erythrocytes, white blood cells or leukocytes, and platelets or thrombocytes. The white blood cells or leukocytes are distinguished from the other types of blood cells in that they have a nucleus. These types of cells have become an area of great interest for disease prevention, including cancer, in recent scientific investigations.

The leukocytes are typically broken down into two types of cells: granulocytes and agranulocytes. The differentiation between these two cell types is the presence of granules in their cytoplasm. The cell types are also distinguished by the shapes of their nucleus as to whether the nucleus is lobed into three segments or non-lobed. One area of great interest recently is a subset of the agranulocytes, which are also known as mononuclear leukocytes, which contains lymphocytes, monocytes and macrophages. The lymphocytes are more common in the lymphatic system, which is part of the circulatory system and a vital part of the immune system, comprising a network of lymphatic vessels that carry a clear fluid called lymph directionally towards the heart. The leukocytes may be further broken down into three main types of cells: B cells, T cells and natural killer cells (NK cells).

T cells, named as such because they mature in the thymus, have been found to play an intricate role in the immune system and disease prevention. For instance, one special type of T cell is known as a Jurkat T cell. This is an immortalized line of cells that are used to study T cell leukemia, T cell signaling, and other types of diseases, particularly HIV.

To study these Jurkat T cells, it is necessary to filter and separate the cells from cell cultures. Various means are utilized for the separation process including centrifugation and physical filter (size exclusion) processes. During these physical separation processes, many of the cells are damaged or destroyed.

It is therefore desirable to utilize a separation and filtration process that does not damage the cells of interest for scientific investigation. In this regard, acoustophoresis is the separation of particles and secondary fluids from a primary or host fluid using high intensity acoustic standing waves, and without the use of membranes or physical size exclusion filters.

BRIEF DESCRIPTION

The present disclosure relates, in various embodiments, to acoustophoretic systems, devices, and methods using multi-dimensional acoustic standing waves to separate particles from a particle/fluid mixture, namely biological cells (e.g., Chinese hamster ovary (CHO) cells, NSO hybridoma cells, baby hamster kidney (BHK) cells, or human cells, T cells, B cells, NK cells, algae, bacteria, viruses, or microcarriers) from a host fluid. More particularly, the devices include a flow chamber to which is coupled an ultrasonic transducer that can be actuated to set up a multi-dimensional acoustic standing wave. The ultrasonic transducer may be used with a reflector to generate the multi-dimensional acoustic standing wave. Two opposing ultrasonic transducers may be used to generate the multi-dimensional acoustic standing wave. An ultrasonic transducer may be used to generate an acoustic wave, as well as to reflect an acoustic wave, which can contribute to generating the multi-dimensional acoustic standing wave Disclosed herein in various embodiments are methods for separating biological cells from a host fluid, comprising: chilling a mixture of the host fluid and the biological cells; and flowing the cooled mixture of the host fluid and the biological cells through a first acoustophoretic device. The first acoustophoretic device comprises: a flow chamber having at least one inlet and at least one outlet; at least one ultrasonic transducer coupled to the flow chamber to permit a multi-dimensional acoustic standing wave to be generated in the flow chamber by the at least one ultrasonic transducer. The at least one ultrasonic transducer includes a piezoelectric material configured to be driven to create a multi-dimensional acoustic standing wave in the flow chamber. A reflector across the flow chamber from the at least one ultrasonic transducer is provided to reflect an ultrasonic signal to contribute to generating the multi-dimensional acoustic standing wave in the flow chamber. A first signal is sent to the first acoustophoretic device to drive the at least one ultrasonic transducer to create the multi-dimensional standing wave. At least some of the biological cells are trapped in the standing wave, and then agglomerate, aggregate, clump, or coalesce together, and subsequently settle out of the host fluid due to enhanced gravitational settling forces. The settled clusters may exit the flow chamber via the at least one outlet.

The biological cells can be Jurkat T cells, or can be T cells having a low ribosomal content of less than 30 wt % (dry mass fraction of the cell).

During the chilling step, the mixture can be chilled to a temperature of about 20° C. to about 25° C. Alternatively, the chilling can lower the temperature of the mixture by from about 10° C. to about 20° C.

In specific embodiments, the at least one outlet of the device includes a concentrate outlet that is located at a bottom end of the flow chamber for recovering the biological cells; and the first acoustophoretic device also includes a permeate outlet located at a top end of the flow chamber. In some such embodiments, the host fluid and biological cells exiting the permeate outlet of the first acoustophoretic device can be sent to an inlet of a second acoustophoretic device. This is a "dual-pass" acoustophoretic system.

The mixture may be flowed into the first acoustophoretic device at a flow rate such that the mixture has a residence of at least 5 minutes. In particular embodiments, the concentrated fluid/cell mixture recovered from the at least one concentrate outlet (i) has a cell concentration of at least two times an original cell concentration of the mixture of the host fluid and the biological cells; and (ii) has a volume of at least one half an original feed volume of the mixture of the host fluid and the biological cells.

Also disclosed herein are acoustophoretic systems for separating biological cells from a mixture of a host fluid and the biological cells, comprising: a means for chilling the mixture; and a first acoustophoretic device. The first acoustophoretic device comprises: a flow chamber having at least one inlet and at least one outlet, the at least one inlet being fluidly connected to the means for chilling; at least one ultrasonic transducer coupled to a side of the flow chamber, the at least one ultrasonic transducer including a piezoelectric material that can be driven to create a multi-dimensional acoustic standing wave in the flow chamber; and a reflector coupled to an opposite side of the flow chamber from the at least one ultrasonic transducer.

The means for chilling the mixture may be a pre-chiller or a fan. This chilling means aids in reducing outgassing that may occur.

In particular embodiments, the at least one inlet of the first acoustophoretic device may be a dump diffuser. Generally, the dump diffuser is used to make the incoming flow more uniform by reducing non-uniformities in the flow chamber resulting from gravity forces, so that the efficiency of the acoustophoretic device is increased or maximized.

The at least one outlet can include a concentrate outlet that is located at a first end of the flow chamber, and the first acoustophoretic device may further include a permeate outlet located at a second end of the flow chamber opposite the first end.

In additional embodiments, the system further comprises a second acoustophoretic device that is generally of the same structure as the first acoustophoretic device, except that the at least one inlet of the second acoustophoretic device is fluidly connected to the permeate outlet of the first acoustophoretic device.

In certain embodiments, a transparent viewing window may be located on a side of the flow chamber opposite the at least one inlet.

Dual-pass acoustophoretic systems for separating biological cells from a mixture of a host fluid and the biological cells are also disclosed. In this way, the acoustophoretic devices of the present disclosure can be incorporated into acoustophoretic systems in which the devices are arranged in series to create a filter "train." The systems can therefore be considered dual- or multi-pass/multi-stage systems. The use of multiple stages of acoustic filtration reduces the burden on subsequent filtration stages and provides for (i) better clarification of the fluid and (ii) better separation of cells from the fluid. This permits recovery of the cells and/or the clarified fluid, as desired.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 15A illustrates the trapping line configurations for seven peak amplitudes of an ultrasonic transducer of the present disclosure. FIG. 15B is a perspective view generally illustrating a device of the present disclosure. The fluid flow direction and the trapping lines are shown. FIG. 15C is a view from the fluid inlet along the fluid flow direction (arrow 161) of FIG. 15B, showing the trapping nodes of the standing wave where particles would be captured. FIG. 15D is a view taken through the transducers face at the trapping line configurations, along arrow 163 as shown in FIG. 15B.

DETAILED DESCRIPTION

Figure 1:
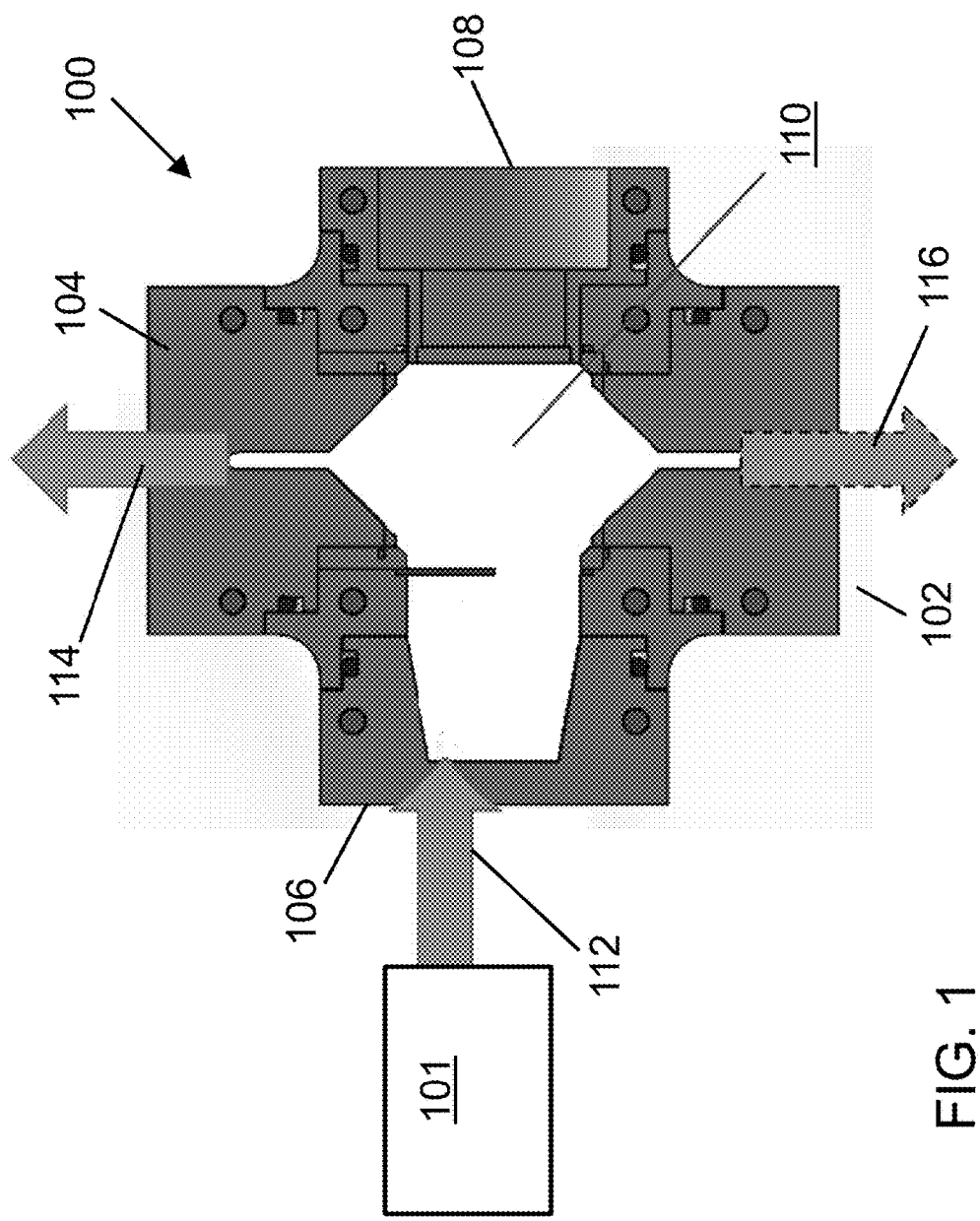
FIG. 1 is a cross-sectional illustration of an exemplary acoustophoretic system according to the present disclosure, incorporating a pre-chiller and one acoustophoretic device.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application refers to "the same order of magnitude." Two numbers are of the same order of magnitude if the quotient of the larger number divided by the smaller number is a value that is at least 1 and less than 10.

Acoustophoresis is a low-power, no-pressure-drop, no-clog, solid-state approach to particle removal from fluid dispersions: i.e., it is used to achieve separations that are more typically performed with porous filters, but it has none of the disadvantages of filters. In particular, the acoustophoretic devices of the present disclosure are suitable for use with bioreactors and operate at the macro-scale for separations in flowing systems with high flow rates. The acoustophoretic devices are designed to create a high intensity multi-dimensional ultrasonic standing wave that results in an acoustic radiation force that is larger than the combined effects of fluid drag and buoyancy or gravity, and is therefore able to trap (i.e., hold stationary) the suspended phase (i.e.

cells) to allow more time for the acoustic wave to increase particle concentration, agglomeration and/or coalescence. This is an important distinction from previous approaches where particle trajectories were merely altered by the effect of the acoustic radiation force. As a result, in the present devices, the radiation force acts as a filter that prevents targeted particles (e.g., biological cells) from crossing the plane of the standing wave. The trapping capability of a standing wave may be varied as desired, for example by varying the flow rate of the fluid, the acoustic radiation force, and the shape of the acoustophoretic device to maximize cell retention through trapping and settling. This technology offers a green and sustainable alternative for separation of secondary phases with a significant reduction in cost of energy. Excellent particle separation efficiencies have been demonstrated for particle sizes as small as one micron. The acoustophoretic devices of the present disclosure have the ability to create ultrasonic standing wave fields that can trap particles in flow fields with a linear velocity ranging from 0.1 mm/sec to velocities exceeding 1 cm/s.

Generally, an acoustic standing wave generates pressure minima at locations on the standing wave where the amplitude is minimum and maximum. These are called, respectively, nodes and anti-nodes. These pressure minima nodes and anti-nodes may be utilized to capture materials that are differentiated from the surrounding environment by size, density and compressibility (i.e., the speed of sound through the material). Those materials that collect at the pressure minima nodes are known as having a positive contrast factor. Those materials that collect at the pressure minima anti-nodes are known as having a negative contrast factor.

In a typical experiment, the system is operated such that the particles are trapped in the ultrasonic standing wave, i.e., remain in a stationary position. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force contributes to trapping the particle. The forces acting on the particle may be greater than the combined effect of fluid drag force and gravitational force. For small particles or emulsions, the drag force $F_D$ can be expressed as:

$$\vec{F}_D = 4\pi\mu_f R_P (\vec{U}_f - \vec{U}_P) \left[ \frac{1 + \frac{3}{2}\hat{\mu}}{1 + \hat{\mu}} \right] \quad (1)$$

where $U_f$ and $U_p$ are the fluid and particle velocity, $R_p$ is the particle radius, $\mu_f$ and $\mu_p$ are the dynamic viscosity of the fluid and particle, and $\hat{\mu} = \mu_p/\mu_f$ is the ratio of dynamic viscosities. The buoyancy force $F_B$ is expressed as:

$$F_B = 4/3\pi R_p^3 (\rho_f - \rho_p) g \quad (2)$$

where $R_p$ is the particle radius, $\rho_f$ is the fluid density, $\rho_p$ is the particle density, and g is the universal gravitational constant.

For a particle to be trapped in the ultrasonic standing wave, the force balance on the particle can be assumed to be zero, and therefore an expression for lateral acoustic radiation force $F_{LRF}$ can be found, which is given by:

$$F_{LRF} = F_D + F_B \quad (3)$$

For a particle of known size and material property, and for a given flow rate, this equation can be used to estimate the magnitude of the lateral acoustic radiation force.

The theoretical model that is used to calculate the acoustic radiation force is the formulation developed by Gor'kov, where the primary acoustic radiation force $F_R$ is defined as a function of a field potential U, $F_R = -\nabla(U)$, where the field potential U is defined as $$U = V_O \left[ \frac{\langle p^2(x, y, z) \rangle}{2\rho_f c_f^2} f_1 - \frac{3\rho_f \langle v^2(x, y, z) \rangle}{4} f_2 \right] \quad (4)$$

and $f_1$ and $f_2$ are the monopole and dipole contributions defined by $$f_1 = 1 - \frac{1}{\Lambda \sigma^2} \quad (5)$$

$$f_2 = \frac{2(\Lambda - 1)}{2\Lambda + 1}$$

where $$\sigma = \frac{c_p}{c_f} \quad (6)$$

$$\Lambda = \frac{\rho_p}{\rho_f}$$

$$\beta_f = \frac{1}{\rho_f c_f^2}$$

where p is the acoustic pressure, u is the fluid particle velocity, ^ is the ratio of cell density $\rho_p$ to fluid density $\rho_f$, $\sigma$ is the ratio of cell sound speed $c_p$ to fluid sound speed $c_f$, $V_o = \pi R_p^3$ is the volume of the cell, and < > indicates time averaging over the period of the wave.

For a one dimensional standing wave, where the acoustic pressure is expressed as $$p = A \cos(kx)\cos(\omega t) \quad (7)$$

where A is the acoustic pressure amplitude, k is the wavenumber, and w is the angular frequency. In this case, there is only the axial component of the acoustic radiation force $F_{ARF}$, which is found to be $$F_{ARF} = V_o k X \frac{A^2}{4\rho_f c_f^2} \sin(2kx) \quad (8)$$

where X is the contrast factor given by $$X = \left( \frac{5\Lambda - 2}{1 + 2\Lambda} - \frac{1}{\sigma^2 \Lambda} \right) \quad (9)$$

Particles with a positive contrast factor will be driven to the pressure nodal planes, and particles with a negative contrast factor will be driven to the pressure anti-nodal planes. In this way, the generation of a multi-dimensional acoustic standing wave in a flow chamber results in the creation of tightly packed clusters of particles in the flow chamber, typically corresponding to the location of the pressure nodes or anti-nodes in the standing wave depending on acoustic contrast factor.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for the macro-scale ultrasonic separators discussed herein since particle clusters can grow quite large. A more complex and complete model for acoustic radiation forces without any restriction as to particle size relative to wavelength was therefore used. The models that were implemented are based on the theoretical work of Yurii Ilinskii and Evgenia Zabolotskaya as described in AIP Conference Proceedings, Vol. 1474-1, pp. 255-258 (2012) and "Acoustic radiation force of a sphere without restriction to axisymmetric fields," Proceedings of Meetings on Acoustics, Vol. 19, 045004 (2013). These models also include the effect of fluid and particle viscosity, and therefore are a more accurate calculation of the acoustic radiation force.

The density of a cell type is typically dependent upon the organelles that are enclosed within the cell wall. One type of organelle, the ribosome, is particularly dense. High concentration of ribosomes in cells can thus allow for a high contrast factor between the cell and its fluid medium, and thus allow for excellent differentiation and separation by an acoustic standing wave. However, cells with low ribosomal content of less than 30 wt % (dry mass fraction of the cell), such as Jurkat T cells, present a lower contrast factor and thus can be harder to distinguish, acoustically, from the fluid medium in which they are carried.

Cells that have a low contrast factor compared to the fluid in which they are transported are more difficult to separate using an acoustic standing wave. Through specialized perturbations of a piezoelectric material, higher order modes of vibration in the piezoelectric material may be generated. When this piezoelectric material that is perturbed in a multimode fashion is coupled with a reflector, a specialized type of acoustic standing wave, known as a multi-dimensional acoustic standing wave, is generated. In this way, Jurkat T cells may be separated from a fluid medium utilizing a multi-dimensional acoustic standing wave. The Jurkat T cells are generally at lower concentrations than, for example, a CHO cell population with 30 million cells per mL versus a concentration of 1 million cells per mL for the Jurkat T cells. Thus, the low contrast cells, such as Jurkat T cells, in a low population concentration are separated continuously from the fluid media within which they are entrained by utilizing a multi-dimensional acoustic standing wave.

The lateral force of the total acoustic radiation force (ARF) generated by the ultrasonic transducers of the present disclosure is significant and is sufficient to overcome the fluid drag force at linear velocities of up to 1 cm/s and beyond. This lateral ARF can thus be used to continuously trap cells in the standing wave, thereby causing the cells to agglomerate, aggregate, clump, or coalesce together, and subsequently settle out of the fluid due to enhanced gravitational forces or rise out of the fluid due to enhanced buoyancy. This lateral ARF can also be used to retain cells in a bioreactor while the bioreactor process continues, which is especially true for a perfusion bioreactor. Additionally, as explained above, this action of the acoustic forces (i.e., lateral and axial acoustic forces) on the trapped particles results in formation of tightly packed clusters through concentration, agglomeration and/or coalescence of particles that settle through enhanced gravity (particles heavier than the host fluid) or buoyancy (particles lighter than the host fluid). Relatively large solids of one material can thus be separated from smaller particles of a different material, the same material, and/or the host fluid through enhanced gravitational separation.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the flow chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component can overcome fluid drag for such clumps of particles to continually grow and then drop out of the mixture due to gravity. Therefore, both the drop in drag per particle as the particle cluster increases in size, as well as the drop in acoustic radiation force per particle as the particle cluster grows in size, may be considered in determining the effectiveness of the acoustic separator device. In the present disclosure, the lateral force component and the axial force component of the multi-dimensional acoustic standing wave are of the same order of magnitude. In this regard, it is noted that in a multi-dimensional acoustic standing wave, the axial force is stronger than the lateral force, but the lateral force of a multi-dimensional acoustic standing wave is much higher than the lateral force of a planar standing wave, usually by two orders of magnitude or more.

Figure 2:
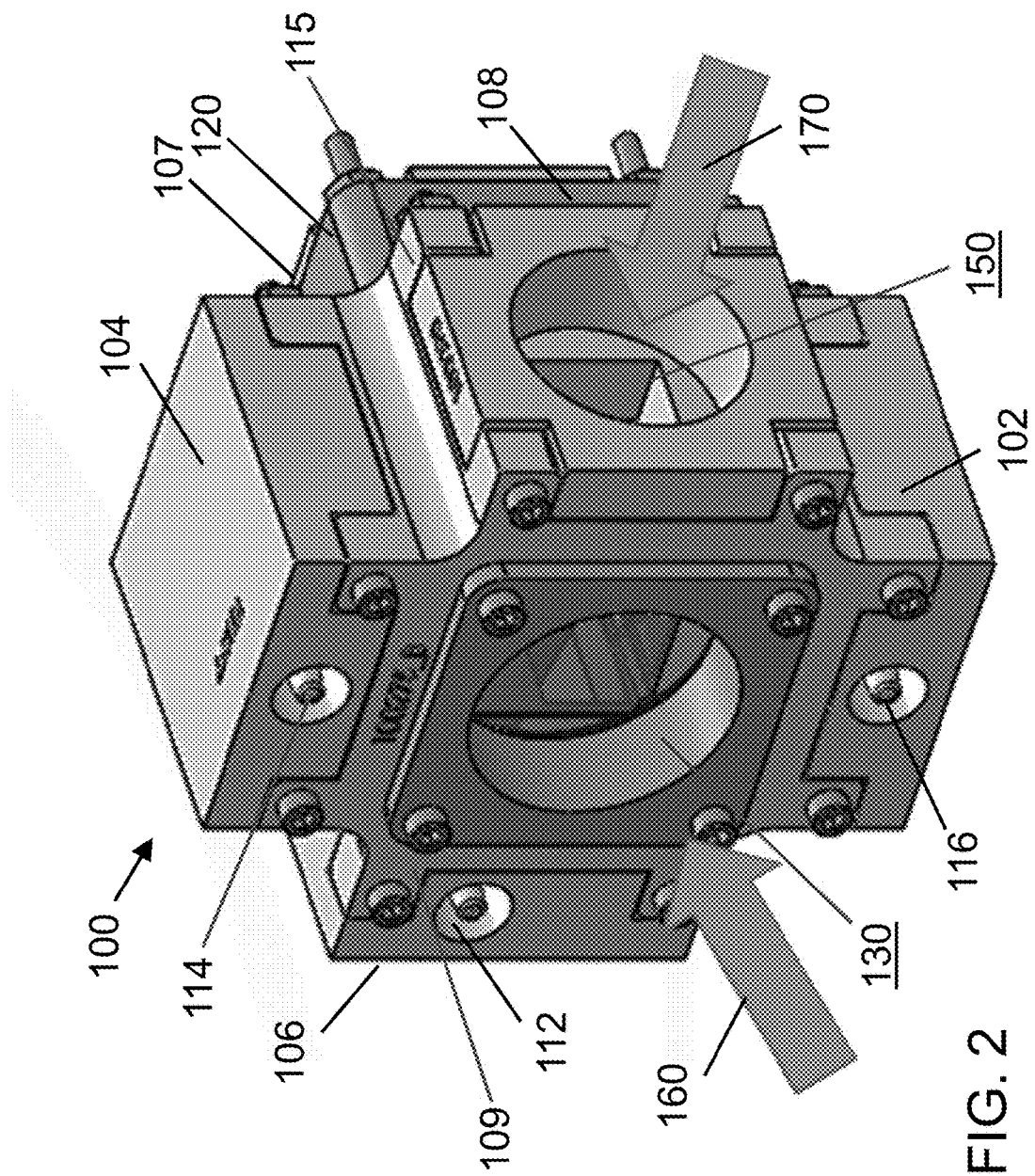
FIG. 2 is a perspective view of the acoustophoretic device of FIG. 1.

With reference now to FIG. 1 and FIG. 2, a first exemplary embodiment of a separation system including a pre-chiller 101 and an acoustophoretic device 100 for acoustic separation of desired target biological cells in a host fluid is depicted. The pre-chiller 101 (i.e. a means for chilling) is used to reduce the temperature of the host fluid/biological cell mixture. The pre-chiller 101 can reduce the temperature of the fluid/cell mixture to about 20° C. to about 25° C., or can reduce the temperature of the fluid/cell mixture from its original temperature by about 10° C. to about 20° C. In this regard, biological cells are typically grown in a bioreactor at body temperature (i.e. about 37° C.), but the acoustophoretic device generates some heat that is absorbed by the fluid/cell mixture, and so the temperature of the incoming mixture is reduced to provide a heat sink.

The acoustophoretic device 100 includes a flow chamber 110 having at least one inlet and at least one outlet. In the embodiment depicted in FIG. 1 and FIG. 2, the flow chamber 110 includes inlet 112, permeate outlet 114, concentrate outlet 116, an ultrasonic transducer 120, and a reflector 130.

The flow chamber 110 is the region of the device 100 through which is flowed an initial mixture of a host fluid and the biological cells. In the embodiment shown in FIG. 1 and FIG. 2, the flow chamber 110 is defined by inlet 112, permeate outlet 114, and concentrate outlet 116. As can be seen in FIG. 1 and FIG. 2, the flow chamber 110 is further defined by a sidewall 115 to which the ultrasonic transducer 120 and the reflector 130 are coupled. As seen here, the sidewall is shaped so that the ultrasonic transducer and reflector are located on opposite sides thereof.

As depicted in FIG. 1 and FIG. 2, the inlet 112 is located along a first side 106 of the flow chamber 110. A transparent viewing window 150 is present on a side of the flow chamber 110 opposite inlet 112 (i.e., at a second side 108 of the flow chamber opposite the first end 106 thereof). A third side 107 of the device houses the ultrasonic transducer 120, while a fourth side 109 of the device, opposite the third side thereof, houses the reflector 130.

In the embodiment depicted in FIG. 1, the concentrate outlet 116 is located at a first end 102 of the device, and the permeate outlet 114 is located at a second end 104 of the flow chamber 100. The concentrate outlet 116 is generally used to recover biological cells from the flow chamber 110. The permeate outlet 114 is generally used to recover the host fluid and residual biological cells from the flow chamber 110. In this regard, the permeate outlet 114 from the flow chamber is located above the ultrasonic transducer 120 and the reflector 130, while the concentrate outlet 116 from the flow chamber is located below the ultrasonic transducer 120 and the reflector 130. While the concentrate outlet 116 and permeate outlet 114 are depicted in FIG. 2 as being on the fourth side 109, but this is not relevant. It is their location relative to the flow chamber 110 that is relevant.

In the embodiment depicted in FIG. 1 and FIG. 2, the device 100 is vertically oriented, such that the first end 102 of the device is the bottom end thereof and the second end 104 of the device is the top end thereof. In this way, the mixture of the host fluid and residual biological cells flows vertically upwards from the flow chamber toward the permeate outlet 114.

The host fluid/biological cell mixture should be flowed into the device 100 at a flow rate such that the mixture has a residence time of at least 5 minutes, or at least 10 minutes. Desirably, the concentrated cell/fluid mixture recovered from the concentrate outlet has a final cell concentration of at least two times the original cell concentration of the original mixture of the host fluid and the biological cells. Desirably, the concentrated cell/fluid mixture recovered from the concentrate outlet also has a volume of at least one half the original feed volume of the original mixture of the host fluid and the biological cells. Put another way, the volume reduction factor (volume of concentrated mixture divided by the volume of the original mixture) is at least two (2), and in further embodiments may be at least four (4).

Figure 3:
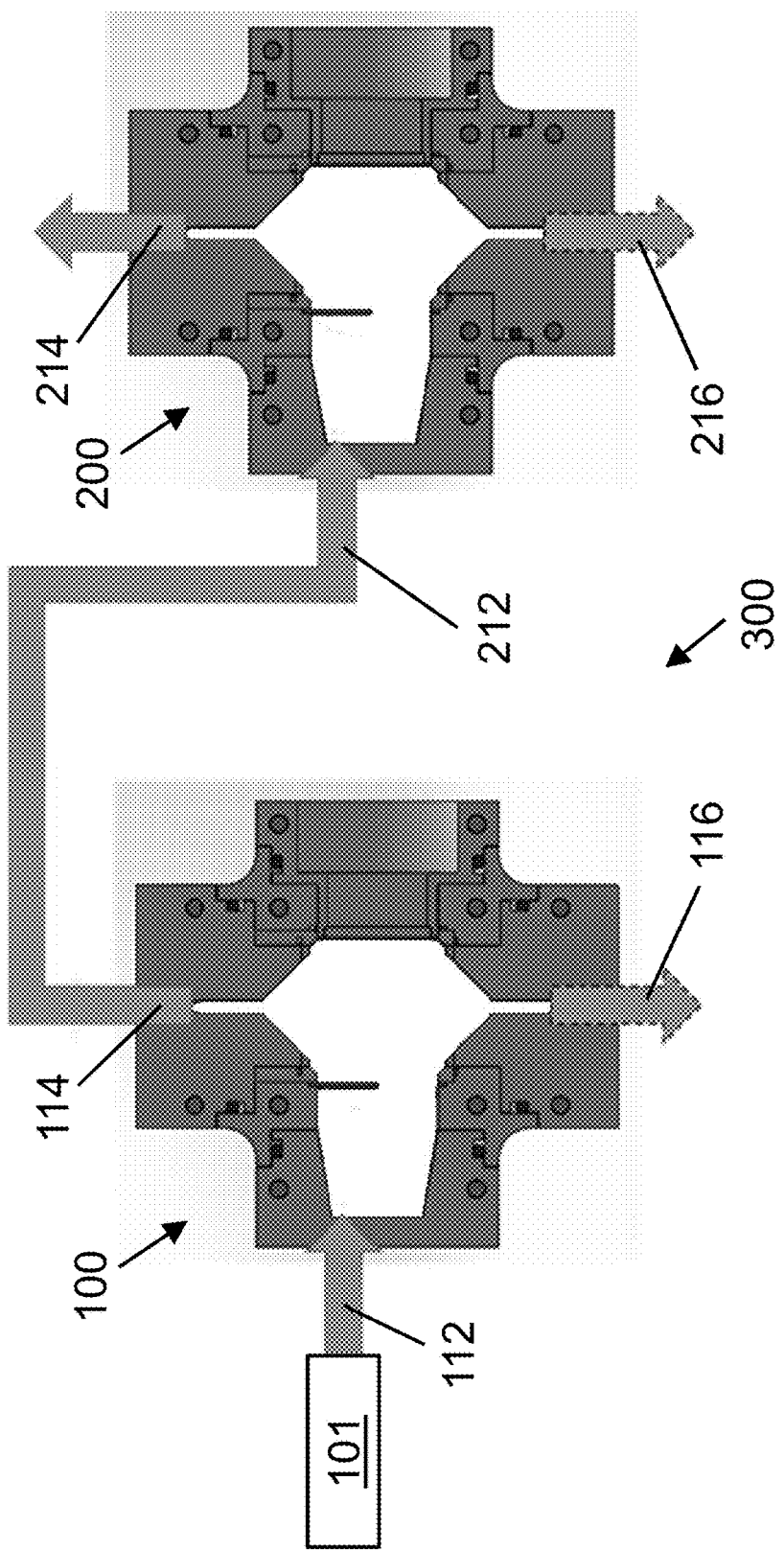
FIG. 3 is a cross-sectional illustration of an exemplary multi-pass acoustophoretic system according to the present disclosure including a pre-chiller and first and second acoustophoretic devices fluidly connected to one another in series. The first acoustophoretic device is as depicted in FIG. 2.

Turning now to FIG. 3, a dual-pass acoustophoretic system 300 is depicted. In the embodiment depicted in FIG. 3, the dual-pass acoustophoretic system 300 includes a pre-chiller 101, a first acoustophoretic device 100 and a second acoustophoretic device 200. The pre-chiller 101 is as previously described with respect to FIG. 1.

Figure 4:
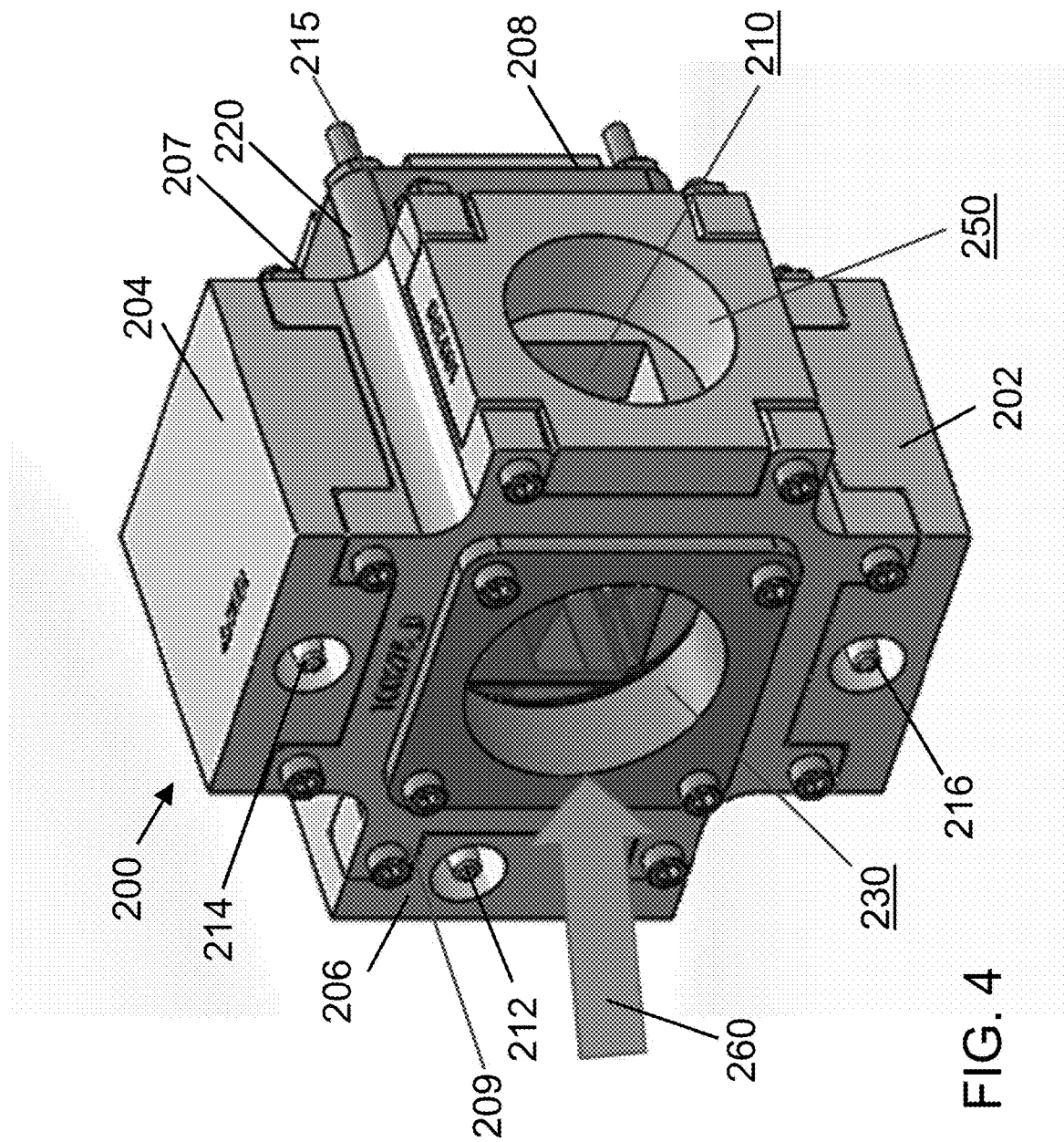
FIG. 4 illustrates an exemplary embodiment of the second acoustophoretic device of the multi-pass acoustophoretic system of FIG. 3.

The first and second acoustophoretic devices 100, 200 are very similar to each other. In particular, each acoustophoretic device includes a flow chamber having an inlet, a first outlet (i.e. concentrate outlet), a second outlet (i.e. permeate outlet), an ultrasonic transducer, and a reflector. Device 100 includes flow chamber 110 having inlet 112, permeate outlet 114, concentrate outlet 116, ultrasonic transducer 120, and a reflector (not shown), and is depicted in FIG. 2. Device 200 is depicted in FIG. 4, and includes flow chamber 210 having inlet 212, permeate outlet 214, sidewall 215, concentrate outlet 216, ultrasonic transducer 220, a reflector 230, and window 250. The sidewall 215 includes a first side 206, a second side 208, a third side 207, and a fourth side 209. In particular, the permeate outlet 114 of the first device 100 is fluidly connected to the inlet 212 of the second device 200, such that the first and second devices are connected in series. In this way, host fluid and any residual biological cells therein that is recovered from the permeate outlet 114 of the first device 100 can be sent to the second device 200 via the inlet 212 thereof for subsequent processing. It is to be understood that dual-pass acoustophoretic system 300 illustrates only two acoustophoretic devices for simplicity, but could be configured to include as many devices/stages as desired.

The frequency/power of the multi-dimensional acoustic standing wave(s) generated by each individual ultrasonic transducer of the system may be varied to capture cells of different sizes, or they may be operated at the same frequency so that the downstream ultrasonic transducer(s) capture additional biological cells that were not captured by an upstream ultrasonic transducer. This permits recovery of the cells and/or the clarified fluid, as desired. In particular embodiments, each transducer in the system is operated at a frequency of about 0.5 megahertz (MHz) to about 4 MHz, including from about 1 MHz to about 2.5 MHz, and from about 2 MHz to about 2.5 MHz.

Prior to discussing further optimization of the devices, it is helpful to provide an explanation now of how multi-dimensional acoustic standing waves are generated. The multi-dimensional acoustic standing wave needed for particle collection is obtained by driving an ultrasonic transducer composed of a piezoelectric material at a frequency that both generates the acoustic standing wave and excites a fundamental 3D vibration mode of the piezoelectric material. The transducer may be composed of various materials that may be perturbed to generate an ultrasonic wave. For example, the transducer may be composed of a piezoelectric material, including a piezoelectric crystal or poly-crystal. Perturbation of the piezoelectric material in an ultrasonic transducer in a multimode fashion allows for generation of a multidimensional acoustic standing wave. A piezoelectric material can be specifically designed to deform in a multi-mode fashion at designed frequencies, allowing for generation of a multi-dimensional acoustic standing wave. The multi-dimensional acoustic standing wave may be generated by distinct modes of the piezoelectric material such as a 3×3 mode that would generate multidimensional acoustic standing waves. A multitude of multidimensional acoustic standing waves may also be generated by allowing the piezoelectric material to vibrate through many different mode shapes. Thus, the piezoelectric material would excite multiple modes such as a 0×0 mode (i.e. a piston mode) to a 1×1, 2×2, 1×3, 3×1, 3×3, and other higher order modes and then cycle back through the lower modes of the piezoelectric material (not necessarily in straight order). This switching or dithering of the piezoelectric material between modes allows for various multidimensional wave shapes, along with a single piston mode shape to be generated over a designated time.

Some further explanation of the ultrasonic transducers used in the devices, systems, and methods of the present disclosure may be helpful as well. In this regard, the transducers may be composed of a piezoelectric material, such as a piezoelectric crystal or poly-crystal, usually made of PZT-8 (lead zirconate titanate). Such crystals may have a 1 inch diameter and a nominal 2 MHz resonance frequency, and may also be of a larger size. Each ultrasonic transducer module can have only one crystal, or can have multiple crystals that each act as a separate ultrasonic transducer and are either controlled by one or multiple amplifiers. The piezoelectric material can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

The transducer can be driven by a signal, such as a voltage signal, a current signal, a magnetic signal, an electromagnetic signal, a capacitive signal, or any other type of signal to which the transducer is responsive to create a multi-dimensional acoustic standing wave in the acoustic chamber. The multi-dimensional acoustic standing wave may be formed with one or more secondary transducers that have an active portion that is directed to another transducer to generate an acoustic standing wave through their interactive operation. For example, the frequency, phase, amplitude or other parameters of the transducers may be controlled to cooperatively generate an acoustic standing wave therebetween. Such an acoustic standing wave may result from constructive/destructive interference between the acoustic waves generated by the respective transducers.

Figure 10:
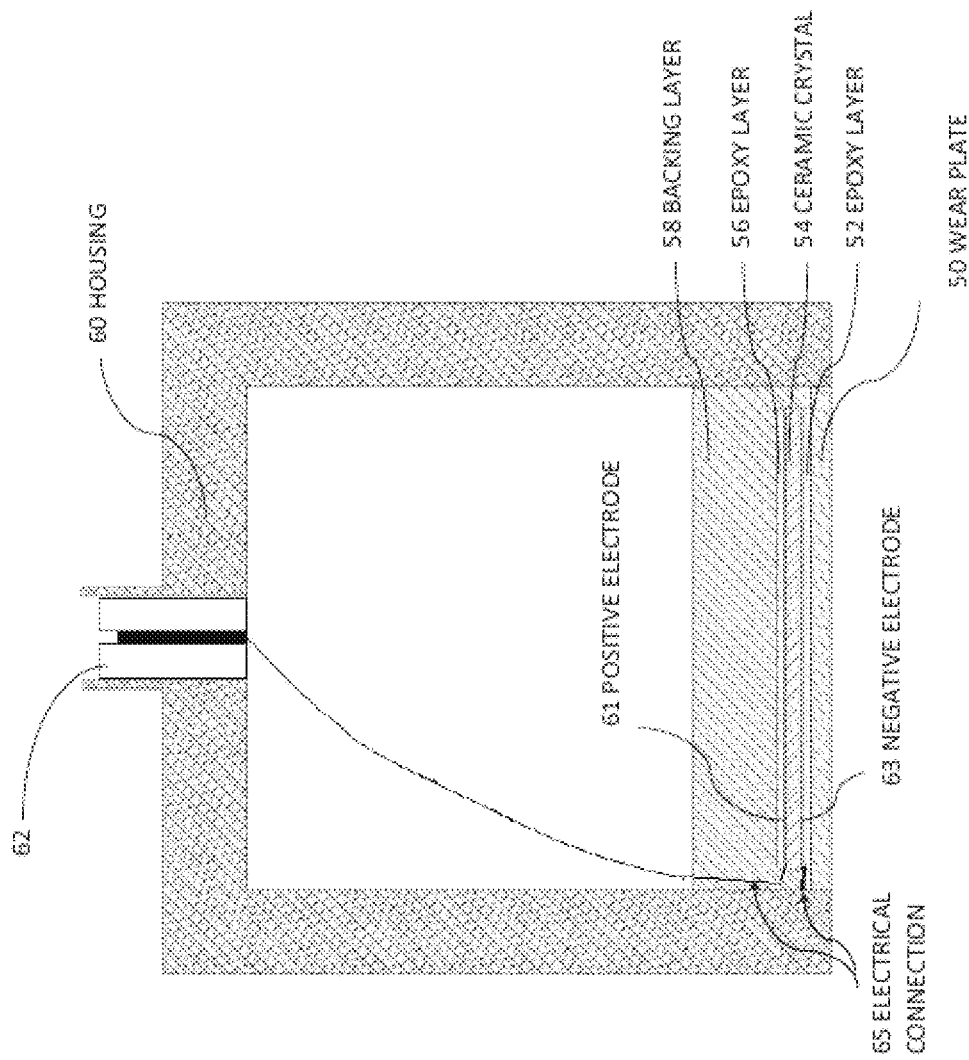
FIG. 10 is a cross-sectional diagram of a conventional ultrasonic transducer.

FIG. 10 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 11:
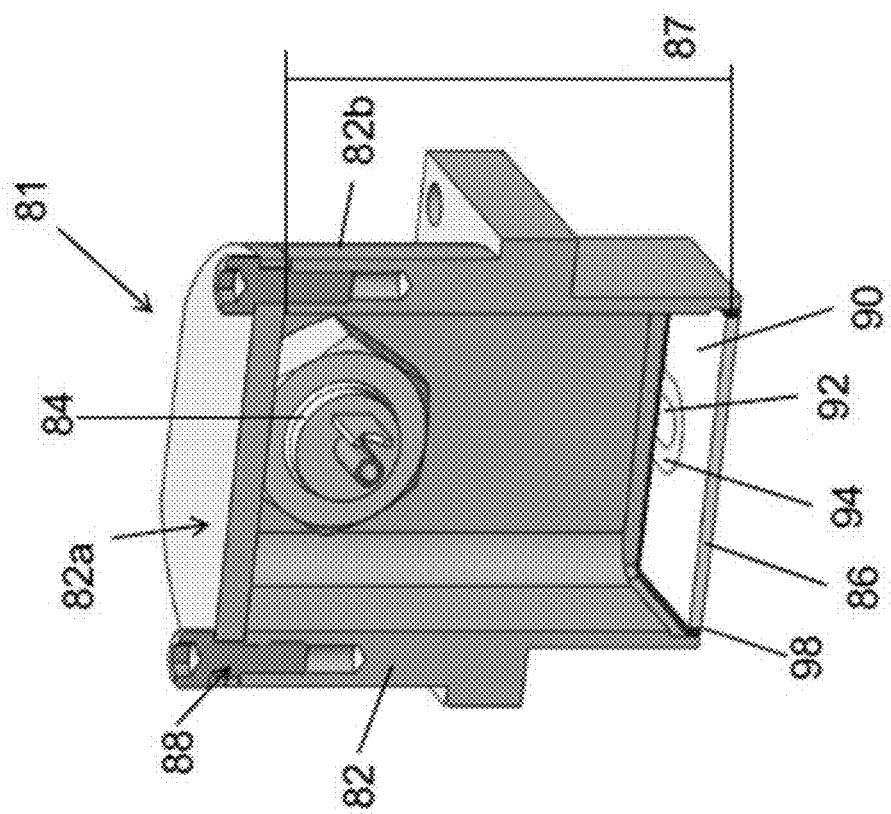
FIG. 11 is a cross-sectional diagram of an ultrasonic transducer of the present disclosure. An air gap is present within the transducer, and no backing layer or wear plate is present.

FIG. 11 is a cross-sectional view of an ultrasonic transducer 81 of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and O2− ions. As an example, a PZT (lead zirconate titanate) crystal 86 defines the bottom end of the transducer, and is exposed from the exterior of the housing. The crystal has an interior surface and an exterior surface. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 12:
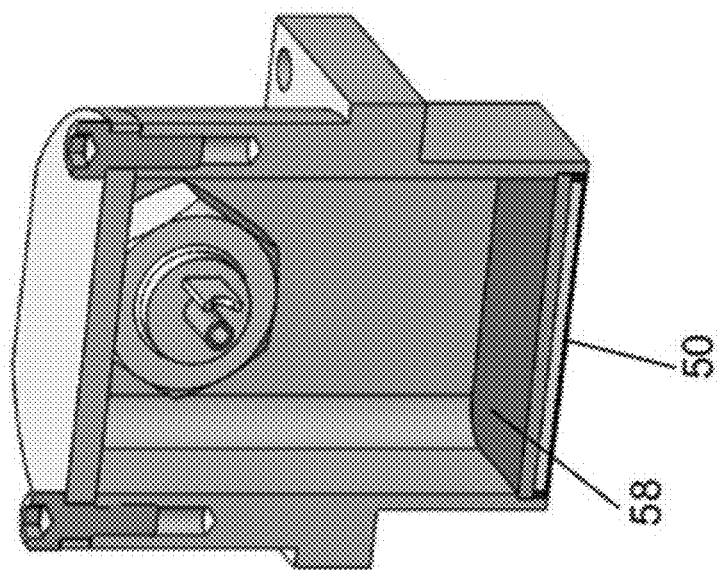
FIG. 12 is a cross-sectional diagram of an ultrasonic transducer of the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 (on the interior surface) and/or wear plate 50 (on the exterior surface) may be provided in some embodiments, as seen in FIG. 12.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes (i.e. near eigenfrequency) with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the piezoelectric material/crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

Figure 13:
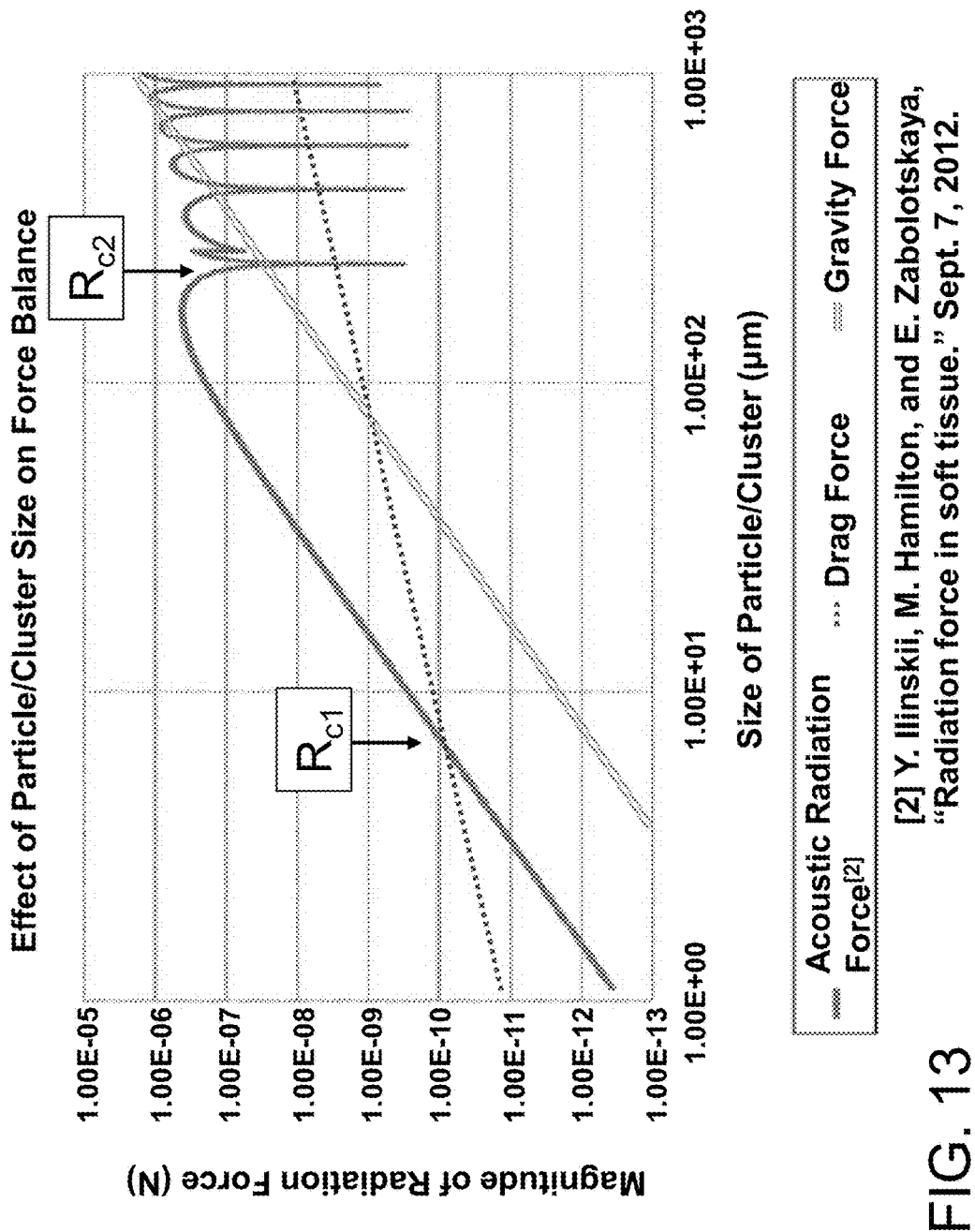
FIG. 13 is a graph showing the relationship of the acoustic radiation force, gravity/buoyancy force, and Stokes' drag force to particle size. The horizontal axis is in microns (μm) and the vertical axis is in Newtons (N).

FIG. 13 is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. The buoyancy force is a particle volume dependent force, and is therefore negligible for particle sizes on the order of micron, but grows, and becomes significant for particle sizes on the order of hundreds of microns. The fluid drag force (Stokes drag force) scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 13, this happens at a particle size labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As particles cluster, the total drag on the cluster is much lower than the sum of the drag forces on the individual particles. In essence, as the particles cluster, they shield each other from the fluid flow and reduce the overall drag of the cluster. As the particle cluster size grows, the acoustic radiation force reflects off the cluster, such that the net acoustic radiation force decreases per unit volume. The acoustic lateral forces on the particles may be greater than the drag forces to permit the clusters to remain stationary and grow in size.

Particle size growth continues until the buoyancy force becomes dominant, which is indicated by a second critical particle size, $R_{c2}$. The buoyancy force per unit volume of the cluster remains constant with cluster size, since it is a function of the particle density, cluster concentration and gravity constant. Therefore, as the cluster size increases, the buoyancy force on the cluster increases faster than the acoustic radiation force. At the size $R_{c2}$, the particles will rise or sink, depending on their relative density with respect to the host fluid. At this size, acoustic forces are secondary, gravity/buoyancy forces become dominant, and the particles naturally drop out or rise out of the host fluid. Not all particles will drop out, and those remaining particles and new particles entering the flow chamber will continue to move to the three-dimensional nodal locations, repeating the growth and drop-out process. This phenomenon explains the quick drops and rises in the acoustic radiation force beyond size $R_{c2}$. Thus, FIG. 13 explains how small particles can be trapped continuously in a standing wave, grow into larger particles or clumps, and then eventually will rise or settle out because of increased buoyancy force.

The size, shape, and thickness of the transducer determine the transducer displacement at different frequencies of excitation, which in turn affects particle separation efficiency. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 14:
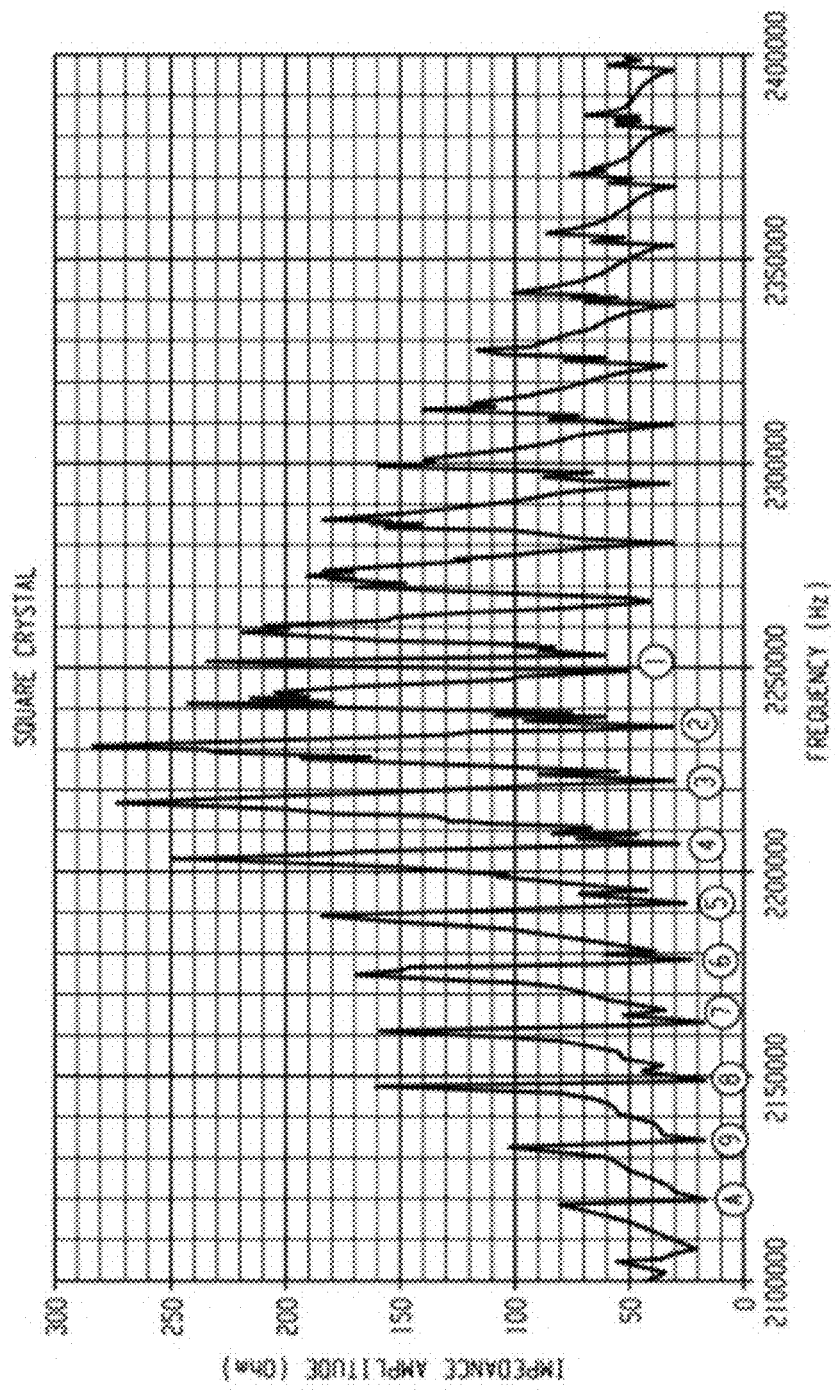
FIG. 14 is a graph of electrical impedance amplitude versus frequency for a square transducer driven at different frequencies.

FIG. 14 shows the measured electrical impedance amplitude of the transducer as a function of frequency in the vicinity of the 2.2 MHz transducer resonance. The minima in the transducer electrical impedance correspond to acoustic resonances of a water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. Higher order transducer displacement patterns result in higher trapping forces and multiple stable trapping lines for the captured particles.

To investigate the effect of the transducer displacement profile on acoustic trapping force and particle separation efficiencies, an experiment was repeated ten times, with all conditions identical except for the excitation frequency. Ten consecutive acoustic resonance frequencies, indicated by circled numbers 1-9 and letter A on FIG. 14, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 15A, for seven of the ten resonance frequencies identified in FIG. 14.

FIG. 15B shows an isometric view of the device in which the trapping line locations are being determined. FIG. 15C is a view of the device as it appears when looking down the inlet, along arrow 161. FIG. 15D is a view of the device as it appears when looking directly at the transducer face, along arrow 163.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines. It is noted that although the different trapping line profiles shown in FIG. 15A were obtained at the frequencies shown in FIG. 14, these trapping line profiles can also be obtained at different frequencies.

FIG. 15A shows the different crystal vibration modes possible by driving the crystal to vibrate at different fundamental frequencies of vibration. The 3D mode of vibration of the crystal is carried by the acoustic standing wave across the fluid in the chamber all the way to the reflector and back. The resulting multi-dimensional standing wave can be thought of as containing two components. The first component is a planar out-of-plane motion component (uniform displacement across crystal surface) of the crystal that generates a standing wave, and the second component is a displacement amplitude variation with peaks and valleys occurring in both lateral directions of the crystal surface. Three-dimensional force gradients are generated by the standing wave. These three-dimensional force gradients result in lateral radiation forces that stop and trap the particles with respect to the flow by overcoming the viscous drag force. In addition, the lateral radiation forces are responsible for creating tightly packed clusters of particles. Therefore, particle separation and gravity-driven collection depends on generating a multi-dimensional standing wave that can overcome the particle drag force as the mixture flows through the acoustic standing wave. Multiple particle clusters are formed along trapping lines in the axial direction of the standing wave, as presented schematically in FIG. 16A.

Figure 16:
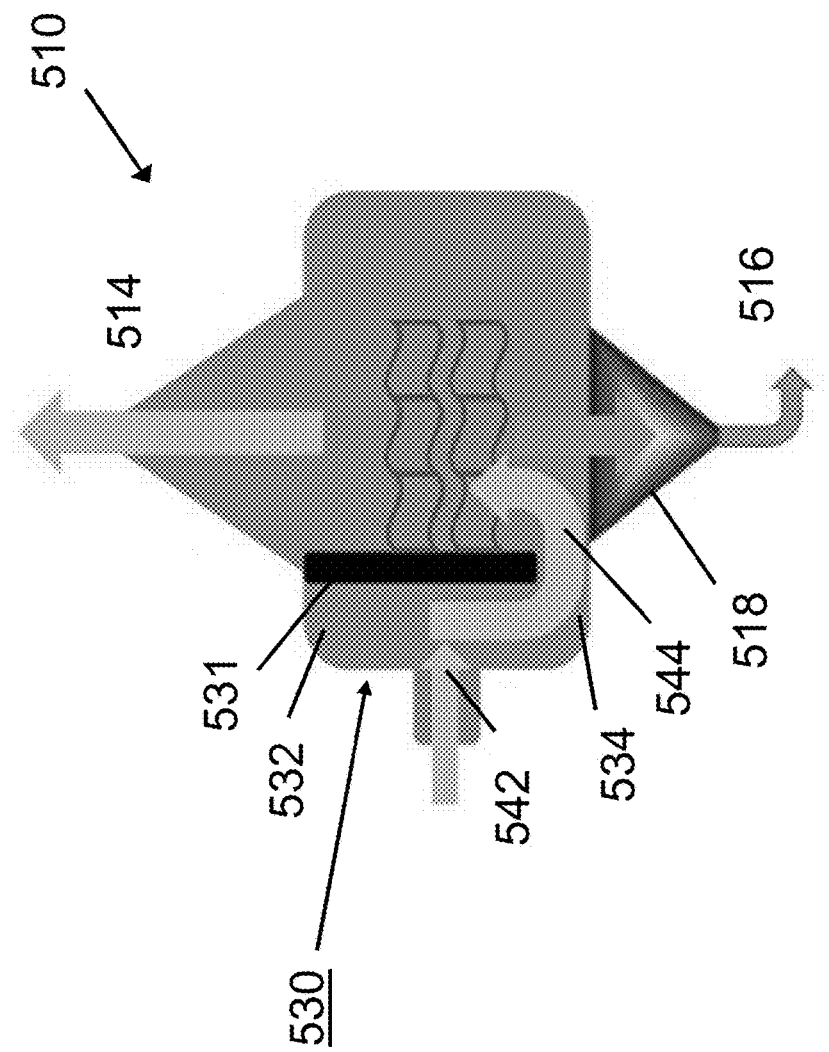
FIG. 16 is a cross-sectional diagram of an acoustophoretic device according to the present disclosure including a flow dump diffuser inlet generating more uniform velocities.

FIG. 16 shows a cross-sectional diagram of an acoustophoretic device 510 as described herein. This device can be used to ameliorate some of the problems with a fluid at low particle Reynolds numbers, and create a more uniform flow through the device. The device 510 has upward, vertical flow through the flow chamber. The flow chamber includes at least one inlet that is a dump diffuser 530 design. Generally, the cross-section of the device in the flow direction is circular or rectangular. The flow chamber is empty, i.e. there is nothing within the chamber, and fluid flows through the flow chamber. A second outlet 514, which is generally used as a permeate outlet to recover host fluid and residual biological cells from the flow chamber, is present at the upper end of the flow chamber. A first outlet 516, which is generally used as a concentrate outlet to recover biological cells from the flow chamber, is present at the lower end of the flow chamber. A shallow wall 518 is present at the lower end of the flow chamber, and leads to the first outlet 516. The shallow wall is angled relative to a horizontal plane, such as the bottom of the flow chamber. At least one ultrasonic transducer (not shown) is present on a sidewall of the flow chamber, and at least one reflector (not shown) is present on the sidewall opposite the ultrasonic transducer.

This device 510 includes a dump diffuser, plenum inlet configuration (i.e., the at least one inlet is a dump diffuser). Where more than one inlet is desired, a second inlet can be provided on the side of the flow chamber opposite the first inlet 530, such that the device would include a symmetrical, dual dump diffuser construction. In such a construction, two dump diffusers 530 would be placed on opposite sides of the device. In FIG. 16, however, the device 510 is depicted as including a single dump diffuser 530. This dump diffuser has a plenum/chamber with an upper end 532 and a lower end 534. The plenum volume provides flow diffusion and dramatically reduces incoming flow non-uniformities. An inlet flow port 542 is located above the lower end 534, and at least one flow outlet 544 is located at the lower end of the plenum. A solid wall 531 is present at the upper end of the plenum. The dump diffuser flow outlet can be a plurality of outlets, such as in the form of slots or a line of holes, and they are placed above the bottom of the flow chamber. The diffusers 530 provide a flow direction normal to the axial direction of the acoustic standing waves generated by the ultrasonic transducer. When multiple flow chamber inlets are desired, the flow chamber inlets are also arranged so that they are in opposing locations, so that the horizontal velocity will decrease to zero in the center of the flow chamber.

The dump diffuser eliminates downward flow in the flow chamber. The mixture fills up the plenum in the dump diffuser and then flows horizontally into the flow chamber, where the mixture flows vertically upwards past the multi-dimensional acoustic standing wave(s). The dump diffuser reduces/eliminates flow pulsations and flow non-uniformities that result from pumps, hosing and horizontal inlet flow where gravity effects dominate. The dump diffuser brings the heavier mixture into the flow chamber below the ultrasonic transducer and the nodal clusters that form in the ultrasonic standing waves. This minimizes any disturbances of the clusters set up by inflowing material.

As previously explained, when a dual dump diffuser construction is desired, the device may be symmetrical about a vertical plane or line of symmetry. This vertical plane or line of symmetry is aligned with gravity forces. Also shown in FIG. 16 are flow streamlines which are desirably symmetrical, since this minimizes non-uniformities, eddy disturbances, circulation, and disturbance of clusters falling through the first outlet 516 to be collected. Symmetry also maximizes gravity forces in the inlet flow distribution and particle collection process. Because it is heavier than the permeate exiting at the top of the device, the (relatively) heavy incoming mixture comes in near the bottom of the flow chamber, spreads out across the bottom of the chamber due to gravity forces, and provides near uniform velocity profiles from bottom to top. The horizontal velocity of the mixture will decrease to zero as it approaches the center of the flow chamber due to the dual opposing inlet flows. This assures minimum interference between the chamber flow and dropping particle clusters. A uniform velocity provides the best separation and collection results because the lateral acoustic forces overcome particle drag to permit the clusters to grow and continuously drop out of the flow chamber. This also eliminates the need for an inlet flow distributor.

As the particle clusters drop out, the axial acoustic forces associated with the standing wave will keep the clusters intact. This assures rapid dropping of the clusters with high terminal velocities, on the order of 1 cm/sec. This is extremely fast compared to the chamber flow velocities, which are on the order of 0.1 cm/sec to 0.3 cm/sec. The shallow wall angle means the cylindrical particle clusters have to drop only a very short distance before they exit the flow chamber, so that little dispersion of the clusters occurs. Ideally, the system operates with 3 to 12 crystal vibration nodes per square inch of transducer. The symmetry, minimum flow disturbance in the central collection region, and shallow collector walls provide good collection without the need for baffles/laminar plates.

Figure 17:
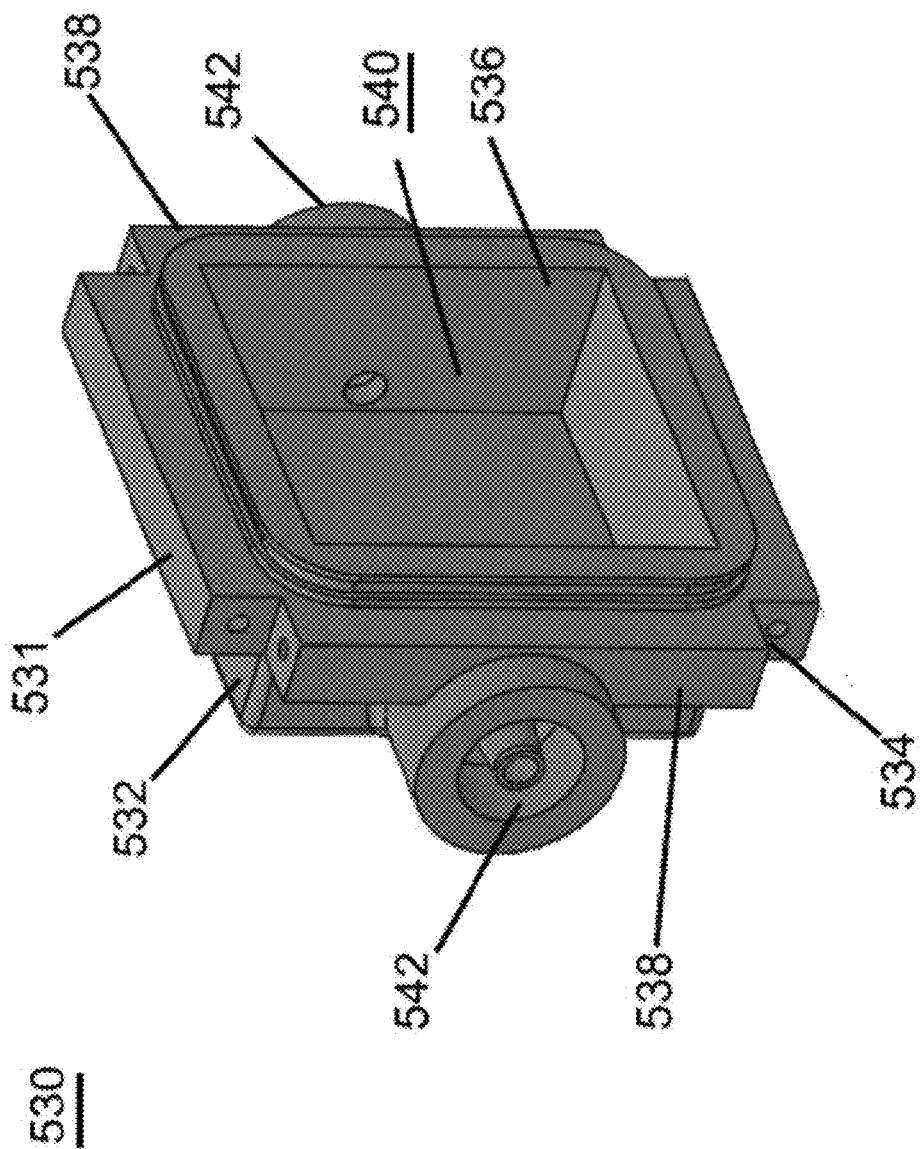
FIG. 17 is a perspective view showing the internal structure of an exemplary dump diffuser.
Figure 18:
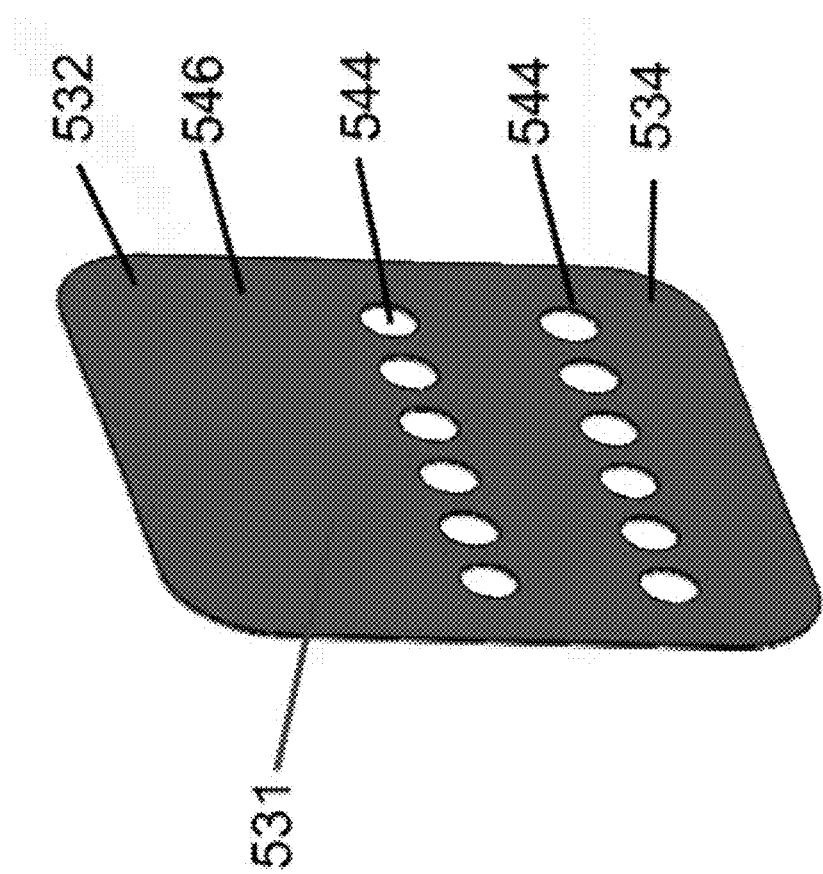
FIG. 18 is a perspective view of a front plate that can be used with the dump diffuser of FIG. 17.

FIG. 17 and FIG. 18 provide additional detail on the dump diffusers that are used for providing a more uniform flow of the mixture of host fluid and particulate into the acoustic chamber 510. FIG. 17 is a perspective view with the front plate removed, showing both the interior and the exterior of a dump diffuser. FIG. 18 is a perspective view of the front plate of the dump diffuser. Starting with FIG. 17, the dump diffuser 530 includes a housing 531 having an upper end 532, an opposite lower end 534, two side faces 538, and a front face 536. A hollow chamber 540 is present within the housing 531. The dump diffuser also includes an entrance port 542 that receives the mixture and leads into the chamber 540. The entrance port 542 is present on the upper end and on a side face 538 of the housing; two entrance ports are visible here. FIG. 18 is a picture of the front plate 546 which is attached to the front face 536 of the housing. As illustrated here, the outlet 544 is located on the lower end 534 and is in the form of two lines of holes, though these could also be in the form of a thin slot. The upper end of the front plate 546 is a solid wall, with no holes therein. In use, the mixture of host fluid/second fluid or particulate enters through entrance ports 542 and fills up the chamber 540. Pressure then pushes the mixture uniformly out through outlets 544.

One specific application for the acoustophoretic devices disclosed herein is in the processing of bioreactor materials. It is important to be able to separate certain cells, such as Jurkat T cells, from other cells in the cell culture. Through the use of acoustophoresis, the separation of the different cell types is very efficient and leads to very little loss of the desired cell types. This is an improvement over current filtration processes (depth filtration, tangential flow filtration, and the like), which show limited efficiencies at high cell densities. The use of acoustophoresis aids in greatly increasing the yield of the bioreactor.

It is contemplated that the acoustophoretic systems/devices of the present disclosure can be used in a filter "train," in which multiple different filtration steps are used to clarify or purify an initial fluid/particle mixture to obtain the desired product and manage different materials from each filtration step. Each filtration step can be optimized to remove a particular material, improving the overall efficiency of the clarification process. An individual acoustophoretic device can operate as one or multiple filtration steps. For example, each individual ultrasonic transducer within a particular acoustophoretic device can be operated to trap materials within a given particle range. It is particularly contemplated that the acoustophoretic device can be used to remove large quantities of material, reducing the burden on subsequent downstream filtration steps/stages. However, it is contemplated that additional filtration steps/stages can be placed upstream or downstream of the acoustophoretic device. Multiple acoustophoretic devices can be used as well. It is particularly contemplated that desirable biomolecules or cells can be recovered/separated after such filtration/purification.

The outlets of the acoustophoretic devices of the present disclosure (e.g. clarified fluid and concentrated cells) can be fluidly connected to any other filtration step or filtration stage. Such filtration steps can include various methods such as depth filtration, sterile filtration, size exclusion filtration, or tangential filtration. Depth filtration uses physical porous filtration mediums that can retain material through the entire depth of the filter. In sterile filtration, membrane filters with extremely small pore sizes are used to remove microorganisms and viruses, generally without heat or irradiation or exposure to chemicals. Size exclusion filtration separates materials by size and/or molecular weight using physical filters with pores of given size. In tangential filtration, the majority of fluid flow is across the surface of the filter, rather than into the filter.

Chromatography can also be used, including cationic chromatography columns, anionic chromatography columns, affinity chromatography columns, mixed bed chromatography columns. Other hydrophilic/hydrophobic processes can also be used for filtration purposes.

The following examples are provided to illustrate the devices and methods of the present disclosure. The examples are merely illustrative and are not intended to limit the disclosure to the materials, conditions, or process parameters set forth therein.

EXAMPLES

Single-Pass System

In FIGS. 5A-8B, various studies were performed using device 100 (see FIG. 2). A fan was used as the pre-chiller. The flow chamber had a volume of 40 mL. The ultrasonic transducer(s) of the device were operated at a frequency of 2.0 MHz to 2.5 MHz A yeast mixture was used in which the mixture was 250 mL of yeast in PBS diluted to $1.00 \times 10^6$ cells/mL. The first outlet 116 had no flow, as the device was drained at the conclusion of testing (i.e. after all of the mixture was run through the device).

Figure 5A:
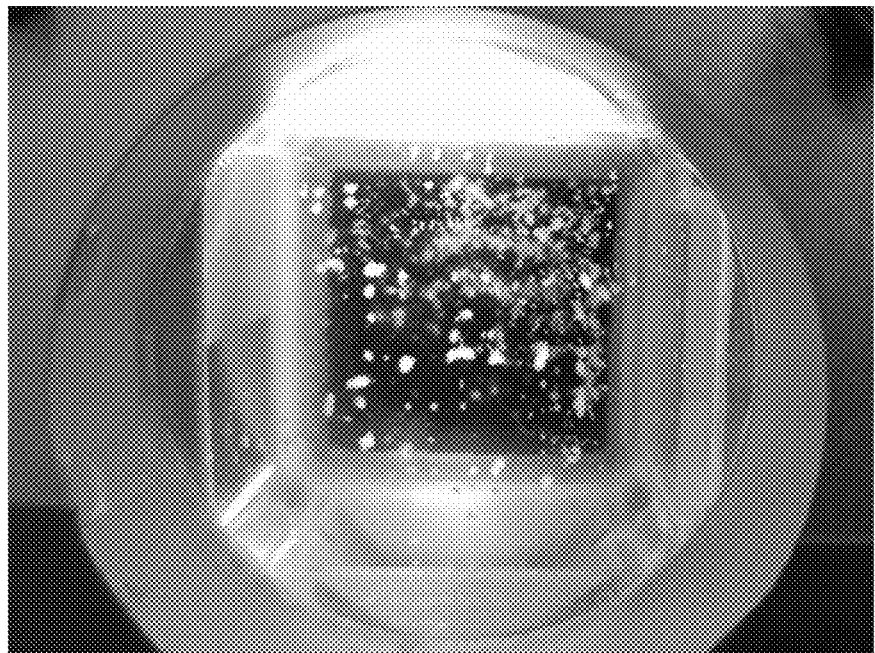
FIG. 5A is a photograph of the flow chamber of the acoustophoretic device of FIG. 1, taken along arrow 160 of FIG. 2. The photograph was taken at a flow rate of 5 mL/min, about 2 minutes into the experiment.
Figure 5B:
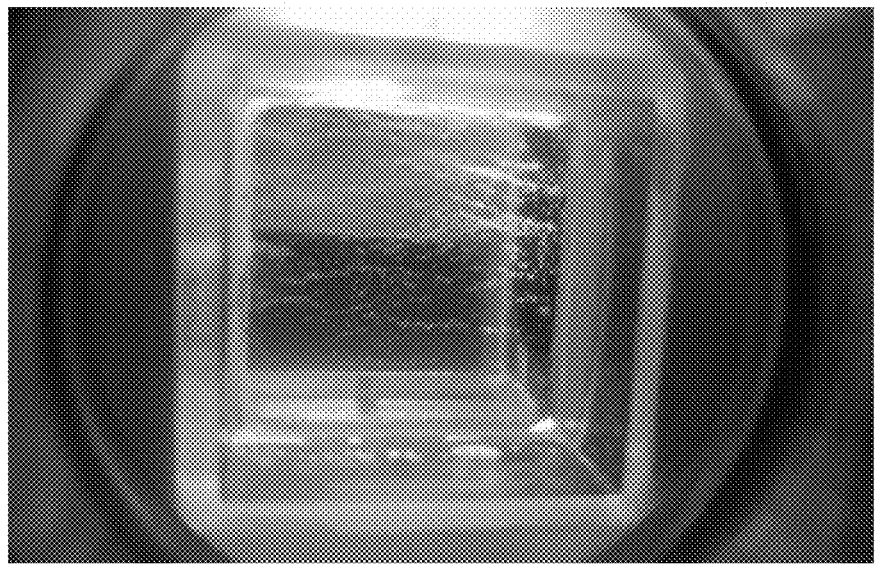
FIG. 5B is a photograph of the flow chamber of the acoustophoretic device of FIG. 1, taken along arrow 170 of FIG. 2. The photograph was taken at a flow rate of 5 mL/min, about 2 minutes into the experiment.

For the study depicted in the photographs of FIG. 5A and FIG. 5B, the yeast mixture was flowed through the device at a flow rate of 5 mL/minute, and the photographs were taken after continuous operation of the device 100 for about two minutes. FIG. 5A is a view of the device as it appears when looking directly at the reflector, along arrow 160 of FIG. 2. FIG. 5B is a view of the device as it appears when looking directly at the viewing window, along arrow 170 of FIG. 2. Capture of the yeast in the mixture due to the acoustic standing wave(s) created by the ultrasonic transducer was instantly observed.

Figure 6A:
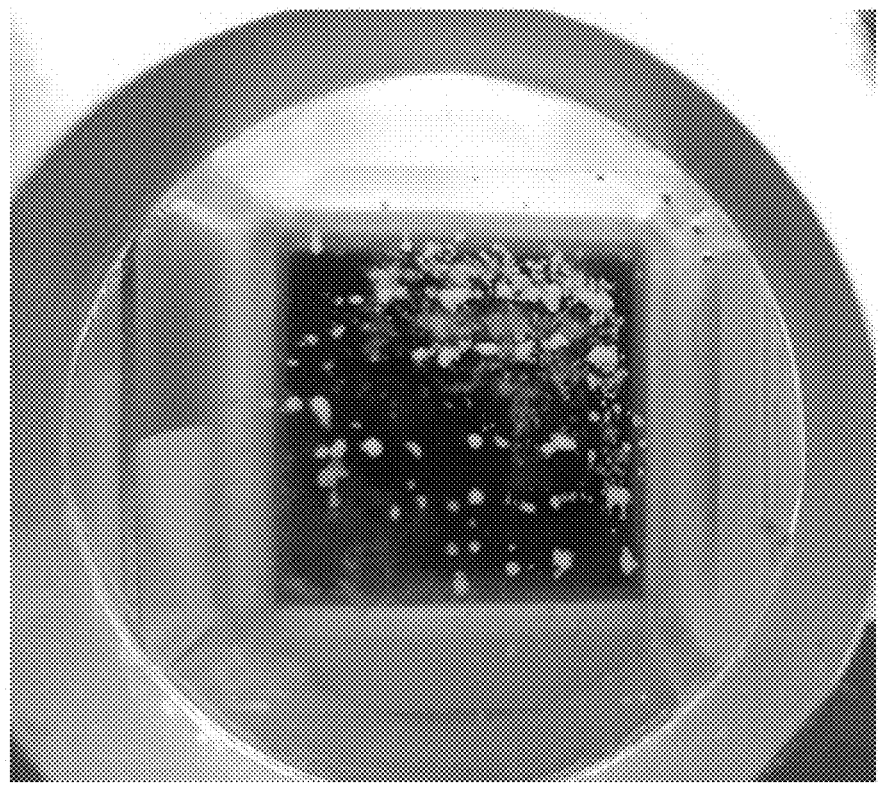
FIG. 6A is a photograph of the flow chamber of the acoustophoretic device of FIG. 1, taken along arrow 160 of FIG. 2. The photograph was taken at a flow rate of 7 mL/min, about 7 minutes into the experiment.
Figure 6B:
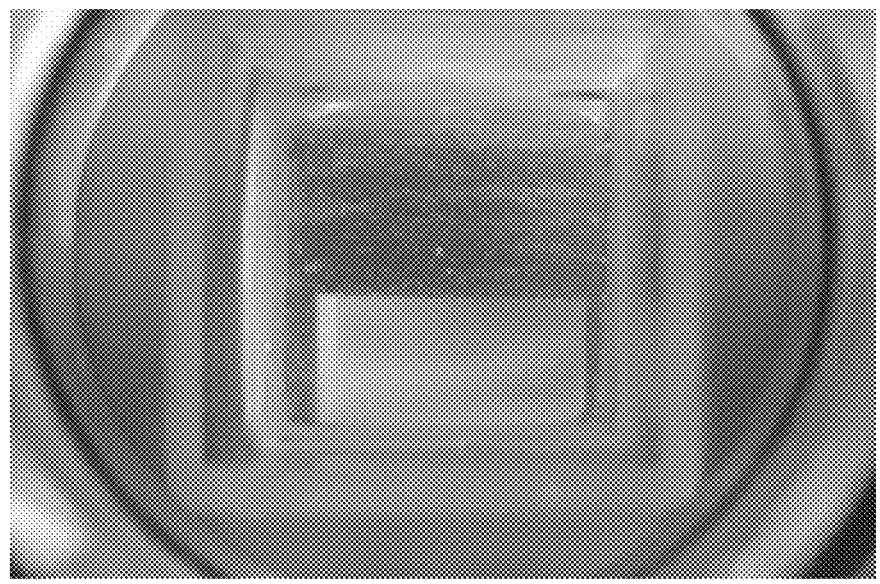
FIG. 6B is a photograph of the flow chamber of the acoustophoretic device of FIG. 1, taken along arrow 170 of FIG. 2. The photograph was taken at a flow rate of 7 mL/min, about 7 minutes into the experiment.

For the study depicted in the photographs of FIG. 6A and FIG. 6B, the yeast mixture was flowed through the device at a flow rate of 7 mL/minute, and the photographs were taken after continuous operation of the device 100 for about seven minutes. FIG. 6A is a view of the device as it appears when looking directly at the reflector, along arrow 160 of FIG. 2. FIG. 6B is a view of the device as it appears when looking directly at the viewing window, along arrow 170 of FIG. 2. In comparison to FIG. 5A and FIG. 5B, a higher order mode on the order of 5×5 was observed in FIG. 6A and FIG. 6B.

In total, three tests were run with the yeast mixture flowed through the device at a flow rate of 5 mL/minute (FIG. 5A and FIG. 5B), and one test was run with the yeast mixture flowed through the device at a flow rate of 7 mL/minute (FIG. 5A and FIG. 5B). All four of the tests showed a volume concentration from 250 mL to 40 mL (i.e., a volume reduction factor of 6.25 times). A summary of these tests is provided in the table below.

| Flow Rate | Cell Retention | Pre-Chiller (if any) |
| --- | --- | --- |
| 5 mL/minute | 48% | None |
| 5 mL/minute | 58% | Fan cooling system |
| 5 mL/minute | 56% | Fan cooling system |
| 7 mL/minute | 61% | |

For the studies depicted in the photographs of FIG. 7A-8B, a mixture was used in which the mixture was 224 mL of Jurkat T-cells in growth media diluted to $0.895 \times 10^6$ cells/mL. The first outlet 116 had no flow, as the device was drained at the conclusion of testing.

Figure 7A:
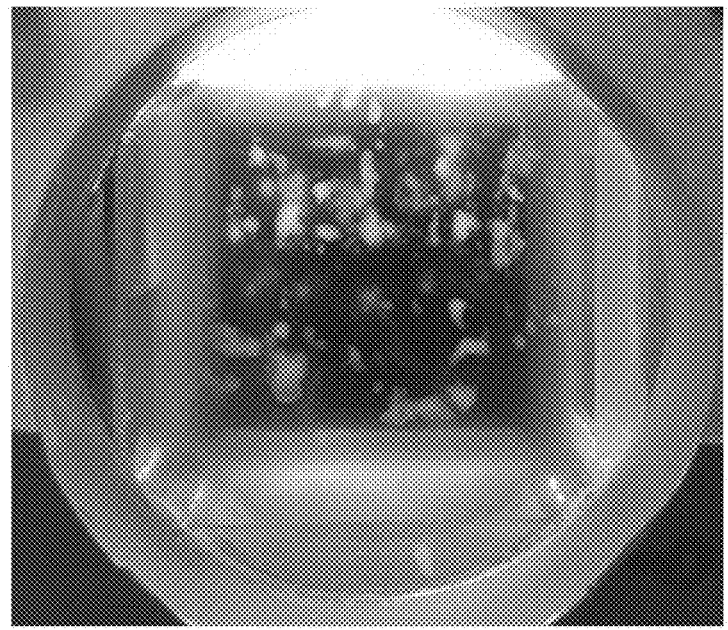
FIG. 7A is a photograph of the flow chamber of the acoustophoretic device of FIG. 1, taken along arrow 160 of FIG. 2. The photograph was taken at a flow rate of 8 mL/min, less than 1 minute into the experiment.
Figure 7B:
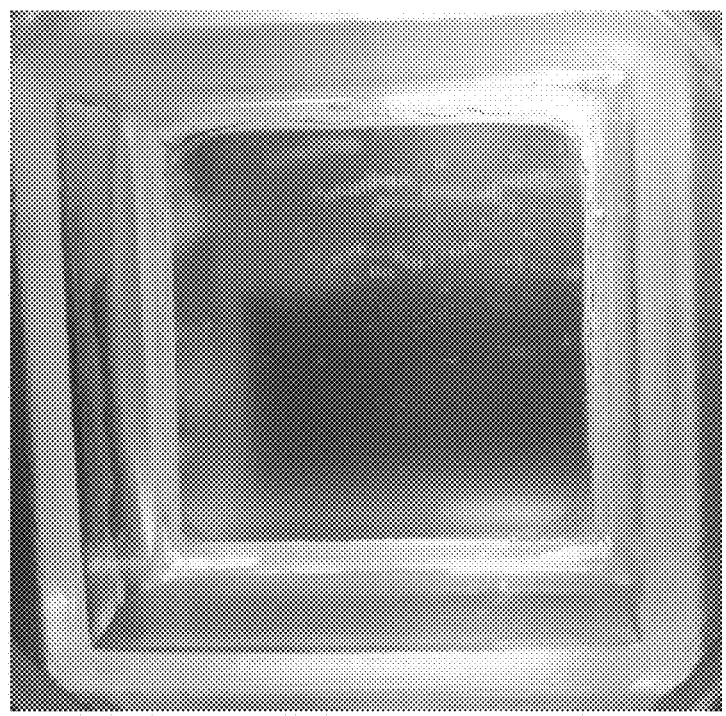
FIG. 7B is a photograph of the flow chamber of the acoustophoretic device of FIG. 1, taken along arrow 170 of FIG. 2. The photograph was taken at a flow rate of 8 mL/min, less than 1 minute into the experiment.
Figure 8A:
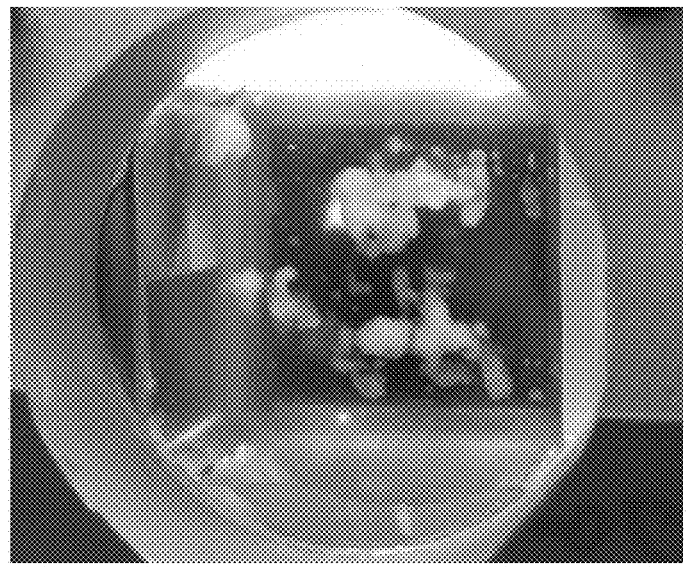
FIG. 8A is a photograph of the flow chamber of the acoustophoretic device of FIG. 1, taken along arrow 160 of FIG. 2. The photograph was taken at a flow rate of 8 mL/min, about 10 minutes into the experiment.
Figure 8B:
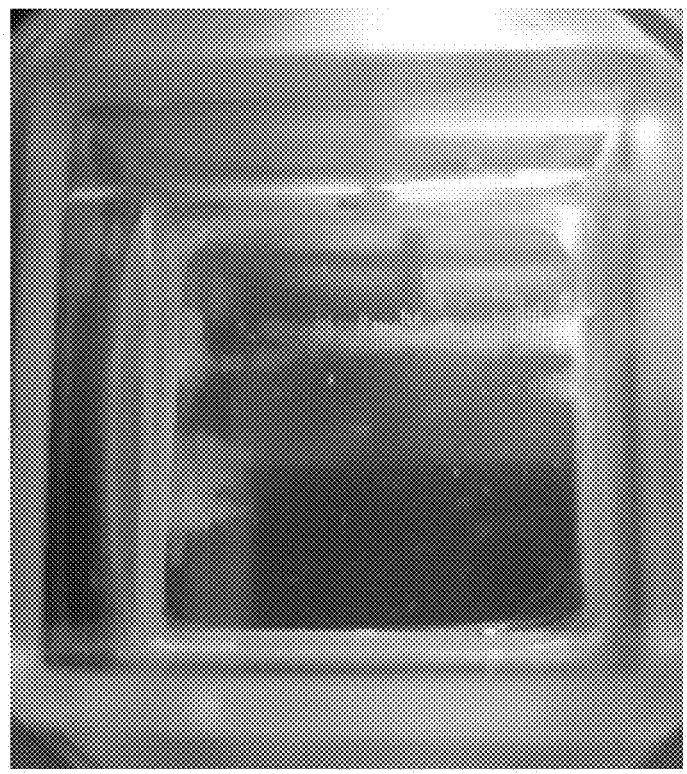
FIG. 8B is a photograph of the flow chamber of the acoustophoretic device of FIG. 1, taken along arrow 170 of FIG. 2. The photograph was taken at a flow rate of 8 mL/min, about 10 minutes into the experiment.

For the study depicted in the photographs of FIG. 7A-8B, the mixture was flowed through the device at a flow rate of 8 mL/minute. The photographs of FIG. 7A and FIG. 7B were taken after continuous operation of the device 100 for less than one minute. The photographs of FIG. 8A and FIG. 8B were taken after continuous operation of the device 100 for about ten minutes. FIG. 7A and FIG. 8A are views of the device as it appears when looking directly at the reflector, along arrow 160 of FIG. 2. FIG. 7B and FIG. 8B are views of the device as it appears when looking directly at the viewing window, along arrow 170 of FIG. 2. These showed a volume reduction factor of 5.7 times. For these tests, a temperature rise from 25° C. to 35° C. was observed, and some minor outgassing occurred at the end of the testing. A summary of these two tests is provided in the table below. It is noted that a small spill during testing led to the large "unaccounted" for percentage.

| | cells/mL | Viability | Volume | Number of Cells |
| --- | --- | --- | --- | --- |
| Feed | $0.895 \times 10^6$ | 81% | 223.98 mL | $200 \times 10^6$ |
| Collected | $2.523 \times 10^6$ | 79% | 39.24 mL | $99.0 \times 10^6$ |
| Permeate | $0.375 \times 10^6$ | 74% | 187.74 mL | $70.5 \times 10^6$ |
| % Collected | | | | 49% |
| % in Permeate | | | | 35% |
| % Unaccounted | | | | 15% |
| Control Sample | | 82% | | |

Dual-Pass System

Figure 9A:
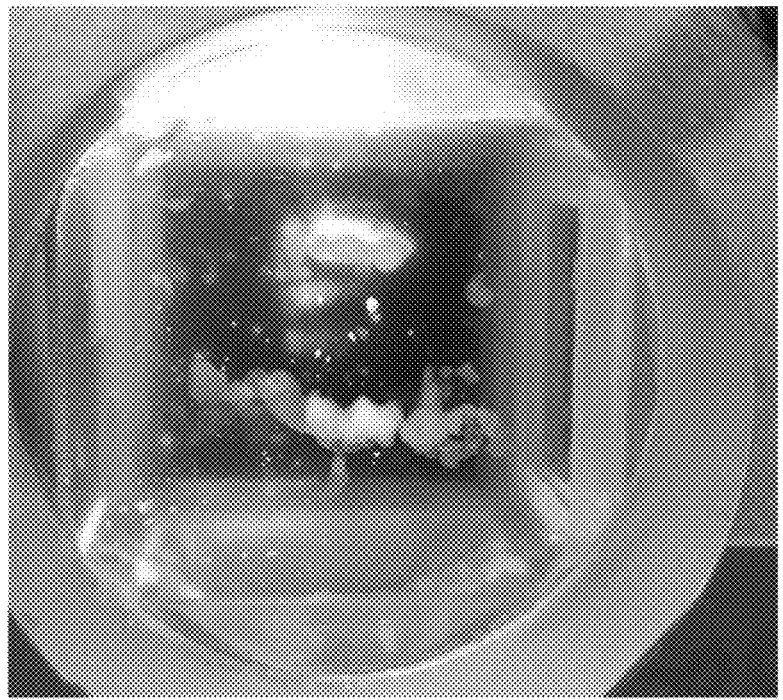
FIG. 9A is a photograph of the flow chamber of the first acoustophoretic device of the multi-pass acoustophoretic system of FIG. 7, taken along arrow 160 of FIG. 2. The photograph was taken at a flow rate of 4 mL/min, about 40 minutes into the experiment.
Figure 9B:
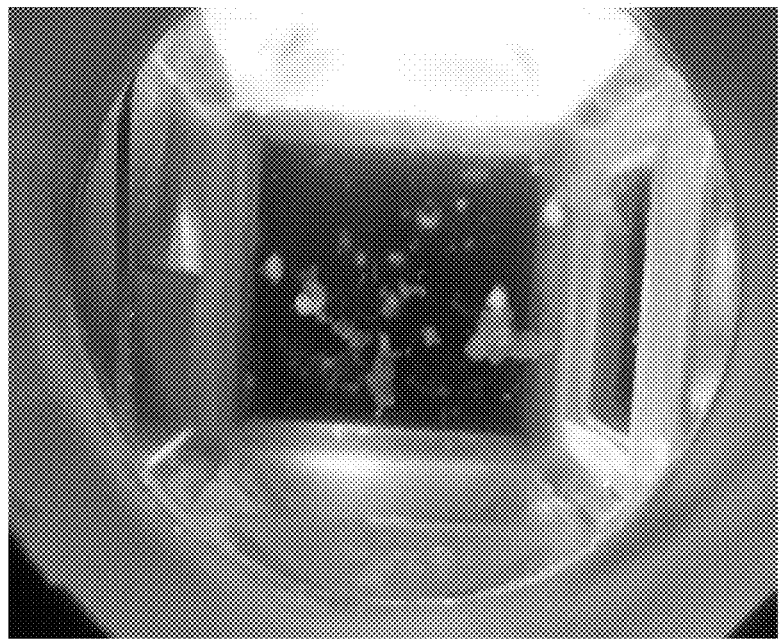
FIG. 9B is a photograph of the flow chamber of the second acoustophoretic device of the multi-pass acoustophoretic system of FIG. 7, taken along arrow 260 of FIG. 4. The photograph was taken at a flow rate of 4 mL/min, about 40 minutes into the experiment.

In FIG. 9A and FIG. 9B, studies were performed using the dual-pass acoustophoretic system 300 of FIG. 3. A mixture was used in which the mixture was 217 mL of Jurkat T-cells in growth media diluted to $0.760 \times 10^6$ cells/mL. The first outlets 116, 216 of the first and second acoustophoretic devices/stages 100, 200 had no flow, as the devices were drained at the conclusion of testing. The ultrasonic transducer(s) of the device were operated at a frequency of 2.0 MHz to 2.5 MHz For the study depicted in the photograph of FIG. 9A, the mixture was flowed through the first device 100 at a flow rate of 4 mL/minute. The photograph of FIG. 9A was taken after continuous operation of the first device 100 for about 40 minutes. FIG. 9A is a view of the first device 100 as it appears when looking directly at the reflector, along arrow 160 of FIG. 2. The first acoustophoretic device 100 of dual-pass acoustophoretic system 300 showed a volume reduction factor of 5.1 times, and a cell concentration factor of 2.9 times. For these tests, a temperature rise from 25° C. to 35° C. was observed, and some minor outgassing occurred at the end of the testing. A summary of the performance of the first device 100 is provided in the table below.

|  | cells/mL | Viability | Volume | Number of Cells |
| --- | --- | --- | --- | --- |
| Feed | $0.760 \times 10^6$ | 78% | 217.21 mL | $165.2 \times 10^6$ |
| Collected | $2.204 \times 10^6$ | 79% | 42.36 mL | $93.3 \times 10^6$ |
| Permeate | $0.345 \times 10^6$ | 71% | 167.65 mL | $57.9 \times 10^6$ |
| % Collected |  |  |  | 57% |
| % in Permeate |  |  |  | 35% |
| % Unaccounted |  |  |  | 8% |
| Control Sample |  | 80% |  |  |

For the study depicted in the photograph of FIG. 9B, the mixture was delivered from the second outlet 114 of the first device 100 to the inlet 212 of the second device 200 and flowed through the second device 200 at a flow rate of 4 mL/minute (i.e., the permeate recovered from the first device 100 was fed to the second device 200). The photograph of FIG. 9B was taken after continuous operation of the second device 200 for about 40 minutes. FIG. 9B is a view of the second device 200 as it appears when looking directly at the reflector, along arrow 260 of FIG. 4. The second acoustophoretic device 200 of dual-pass acoustophoretic system 300 showed a concentration factor of 4.0 times. For these tests, a temperature rise from 25° C. to 35° C. was observed, and some minor outgassing occurred at the end of the testing. A summary of the performance of the second device 200 is provided in the table below.

|  | cells/mL | Viability | Volume | Number of Cells |
| --- | --- | --- | --- | --- |
| Feed | $0.345 \times 10^6$ | 71% | 164.65 mL | $56.8 \times 10^6$ |
| Collected | $0.706 \times 10^6$ | 74% | 41.55 mL | $29.3 \times 10^6$ |
| Permeate | $0.228 \times 10^6$ | 67% | 118.81 mL | $27.1 \times 10^6$ |
| % Collected |  |  |  | 52% |
| % in Permeate |  |  |  | 48% |
| % Unaccounted |  |  |  | 1% |
| Control Sample |  | 83% |  |  |

The results for the first device 100 and the second device 200 of the multi-pass acoustophoretic system 700 were combined, and a summary of the performance of the system 300 is provided in the table below.

|  | cells/mL | Viability | Volume | Number of Cells |
| --- | --- | --- | --- | --- |
| Initial feed | $0.760 \times 10^6$ | 78% | 217.21 mL | $165.2 \times 10^6$ |
| Collected | $2.204 \times 10^6$ | 79% | 42.36 mL | $93.3 \times 10^6$ |
| Permeate | $0.706 \times 10^6$ | 74% | 41.55 mL | $29.3 \times 10^6$ |
| Both devices |  |  | 83.91 mL | $122.7 \times 10^6$ |
| % Collected |  |  |  | 74% |

As can be seen from the table summarizing the performance of the system 300, the dual-pass acoustophoretic system 300 yielded a retention of 74% and a volume reduction factor of 2.6 times (i.e. original feed volume divided final concentrate volume).

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A method for separating biological cells from a host fluid, comprising:
   chilling a mixture of the host fluid and the biological cells;
   flowing the cooled mixture of the host fluid and the biological cells through a first acoustophoretic device, the first acoustophoretic device comprising:
   a flow chamber including at least one inlet and at least one outlet;
   at least one ultrasonic transducer coupled to the flow chamber, the at least one ultrasonic transducer including a piezoelectric material configured to be driven to create a multi-dimensional acoustic standing wave in the flow chamber; and
   a reflector opposite to the at least one ultrasonic transducer; and
   driving the at least one ultrasonic transducer to create the multi-dimensional standing wave in the flow chamber, such that at least some of the biological cells are trapped in the standing wave, and agglomerate, aggregate, clump, or coalesce together, and settle out of the host fluid due to enhanced gravitational settling forces.

2. The method of claim 1, wherein the biological cells are Jurkat T cells, B cells, or NK cells.

3. The method of claim 1, wherein the biological cells are T cells having a low ribosomal content of less than 30 wt %.

4. The method of claim 1, wherein the mixture is chilled to a temperature of about 20° C. to about 25° C.

5. The method of claim 1, wherein the chilling lowers the temperature of the mixture by from about 10° C. to about 20° C.

6. The method of claim 1, wherein the first acoustophoretic device further comprises at least one concentrate outlet located at a bottom end of the flow chamber for recovering the biological cells; and the first acoustophoretic device also further comprises a permeate outlet located at a top end of the flow chamber.

7. The method of claim 6, further comprising sending the host fluid and biological cells exiting the permeate outlet of the first acoustophoretic device to an inlet of a second acoustophoretic device.

8. The method of claim 6, wherein fluid recovered from the at least one concentrate outlet (i) has a cell concentration of at least two times an original cell concentration of the mixture of the host fluid and the biological cells; and (ii) has a volume of at least one half an original feed volume of the mixture of the host fluid and the biological cells.

9. The method of claim 1, wherein the mixture is flowed into the first acoustophoretic device at a flow rate such that the mixture has a residence time of at least 5 minutes.

10. An acoustophoretic system for separating biological cells from a mixture of a host fluid and the biological cells, comprising:
   a chiller for chilling the mixture; and
   a first acoustophoretic device comprising:
      a flow chamber including at least one inlet and at least one outlet, the at least one inlet being fluidly connected to the chiller; and
      at least one ultrasonic transducer coupled to the flow chamber, the at least one ultrasonic transducer including a piezoelectric material configured to be driven to create a multi-dimensional acoustic standing wave in the flow chamber.

11. The system of claim 10, further comprising a reflector opposite to the at least one ultrasonic transducer.

12. The system of claim 10, wherein the chiller for chilling the mixture is a pre-chiller or a fan.

13. The system of claim 10, wherein the at least one inlet of the first acoustophoretic device is a dump diffuser.

14. The system of claim 10, wherein the first acoustophoretic device further comprises at least one concentrate outlet located at a first end of the flow chamber, and wherein the first acoustophoretic device also further comprises a permeate outlet located at a second end of the flow chamber opposite the first end.

15. The system of claim 14, further comprising a second acoustophoretic device comprising:
   a flow chamber including at least one inlet and at least one outlet, the at least one inlet being fluidly connected to the permeate outlet of the first acoustophoretic device;
   at least one ultrasonic transducer coupled to the flow chamber, the at least one ultrasonic transducer including a piezoelectric material configured to be driven to create a multi-dimensional acoustic standing wave in the flow chamber; and
   a reflector opposite to the at least one ultrasonic transducer.

16. A device for separating biological cells from a host fluid, comprising:
   means for chilling a mixture of the host fluid and the biological cells;
   means for flowing the cooled mixture of the host fluid and the biological cells through a first acoustophoretic device;
   means for separating the biological cells from the host fluid using a multi-dimensional acoustic standing wave.

17. The device according to claim 16, further comprising means for collecting the separated biological cells.

18. The device according to claim 16, further comprising means for collecting a permeate.

* * * * *